US007371821B2

(12) United States Patent
Ching et al.

(10) Patent No.: US 7,371,821 B2
(45) Date of Patent: May 13, 2008

(54) **CLONING AND EXPRESSION OF THE FULL LENGTH 110 KDA ANTIGEN OF *ORIENTIA TSUTSUGAMUSHI* TO BE USED AS A VACCINE COMPONENT AGAINST SCRUB TYPHUS**

(75) Inventors: Wei-Mei Ching, Bethesda, MD (US); Chien-Chung Chao, North Bethesda, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 205 days.

(21) Appl. No.: 11/108,867

(22) Filed: Apr. 19, 2005

(65) Prior Publication Data

US 2005/0234005 A1 Oct. 20, 2005

Related U.S. Application Data

(60) Provisional application No. 60/563,447, filed on Apr. 20, 2004.

(51) Int. Cl.

| | |
|---|---|
| ***C07K 1/00*** | (2006.01) |
| ***C07K 2/00*** | (2006.01) |
| ***A61K 39/02*** | (2006.01) |
| ***A61K 38/00*** | (2006.01) |
| ***C12N 15/00*** | (2006.01) |

(52) U.S. Cl. ...................... 530/350; 530/300; 530/825; 424/190.1; 424/234.1; 435/69.3; 435/71.1; 435/320.1; 514/2

(58) Field of Classification Search ................ 530/350, 530/300, 825, 806; 424/190.1, 234, 234.1; 435/320.1, 71.1, 69.3; 514/2
See application file for complete search history.

(56) References Cited

U.S. PATENT DOCUMENTS

2003/0165523 A1* 9/2003 Ching et al. ............ 424/190.1

OTHER PUBLICATIONS

Oaks et al. Infect. Immun. 55: 1156-1162, 1987.*
Mierendorf et al. inNovations 1: 1-3, 1994.*

* cited by examiner

*Primary Examiner*—S. Devi
(74) *Attorney, Agent, or Firm*—Joseph K. Hemby, Jr.; Albert M. Churilla

(57) ABSTRACT

The inventive subject matter relates to a recombinant 110 kDa protein from *O. tsutsugamuchi*, Karp, Kato and Gilliam strains and for a DNA expression system containing DNA encoding the 110 kDa protein of *O. tsutsugamuchi*. The invention also relates to the use of these recombinant contructs in a formulation for the induction of a protective immune response against *O. tsutsugamuchi* invection using. The inventive subject matter also relates to a recombinant 110 kDa *O. tsutsugamuchi* protein or 110 kDa fragments for the production of antigen for use in immunodiagnosistic asssays for scrub typhus.

8 Claims, 1 Drawing Sheet

1 2 3 4 5 6 7 8 9 10 11 12

CLONING AND EXPRESSION OF THE FULL LENGTH 110 KDA ANTIGEN OF *ORIENTIA TSUTSUGAMUSHI* TO BE USED AS A VACCINE COMPONENT AGAINST SCRUB TYPHUS

CROSS REFERENCE TO RELATED APPLICATION

This application claims priority to U.S. Provisional application 60/563,447 filed Apr. 20, 2004.

SEQUENCE LISTING

The disk Labeled "Cloning and expression of the full length 110 kDa antigen of *O. tsutsugamushi* to be used as a vaccine component against scrub typhus" containing the sequence listing file nc96,303.st25 is incorporated by reference. The file contains the same information that is provided in paper form as part of the application.

FIELD OF THE INVENTION

This invention relates to the protection against infection of *Orientia tsutsugamushi.*

DESCRIPTION OF PRIOR ART

Scrub typhus infection is caused by the Gram-negative bacterium *Orientia tsutsugamushi*. It accounts for up to 23% of all febrile episodes in endemic areas of the Asia-Pacific region and can cause up to 35% mortality if left untreated [1,2]. Vaccines offer the potential of long-term prevention of morbidity and mortality from scrub typhus. They also obviate the difficulties posed by vector control and preventative chemoprophylaxis. The recent evidence of antibiotic resistance of *O. tsutsugamushi* further emphasizes the need of a scrub typhus vaccine [3,4,5]. Prior vaccine development efforts using the whole organism have suggested that a scrub typhus vaccine is possible. Immunization of volunteers with live vaccine in combination with tetracycline prophylaxis elicited immunity comparable to that of natural infection [6,7]. A polyvalent gamma irradiated vaccine that elicited some protection against heterologous serologic types was also demonstrated [8]. However due to the difficulties in mass production of purified *O. tsutsumagushi* and its instability upon storage, no useful product which meets today's FDA standards has been provided [9].

Whole-organism vaccines have been previously developed and their protections have been short-lived and lack of cross strain protection. The major surface protein antigen, the variable 56-kDa protein which account for the antigenic variation, has been shown to induce protective immunity against the homologous strain but not the heterologous strains. The fact that other antigens, such as 110, 47 and 22 kDa have also been identified with high seroreactivity suggests that a combination of several of these antigens may provide better protection against various stains of *O. tsutsugamushi* infection [10].

Although vaccination with a DNA construct or a recombinant protein of the major outer membrane protein 56 kDa antigen has been shown to provide protection against homologous challenge, complete cross protection from heterologous challenge has not been obtained. A minor 110 kDa antigen is also recognized by patient sera, suggesting it may provide additional protection against the *O. tsutsugamushi* infection. In order to develop a better and broadly protective vaccine candidate, we have successfully cloned the gene coding for the whole ORF of 110 kDa protein from major *O. tsutsugamushi* strains, including Karp, Kato and Gilliam into an expression system in order to generate a potential DNA vaccine candidate. Evaluation of the efficacy of the DNA constructs as potential vaccine formulations was also conducted in mice with or without either IL-2 or GM-CSF as adjuvant. Co-immunization with Karp containing DNA construct and pGM-CSF provided 60% protection whereas co-immunization with IL-2 afforded much less protection. These results suggest that the DNA expression system, alone or with GM-CSF, is useful in vaccine formulations against *O. tsutsugamushi* infection and as a prophylactic against scrub typhus.

SUMMARY OF THE INVENTION

Accordingly, an object of this invention is a recombinant construct and expressed polypeptide possessing immunogenic regions.

Another object of the invention is an expression system for expressing the *O. tsutsugamushi* 110 kDa protein comprising cloning and amplifying the DNA sequence encoding the *O. tsutsugamushi* 110 kDa protein and inserting and ligating the digestion product into a suitable expression system wherein the protein is expressed.

Still another object of the invention is an immunogenic composition comprising a plasmid expressing the DNA sequence encoding an *O. tsutsugamushi* strain 110 kDa protein, wherein the protein is expressed and a plasmid expressing the DNA sequence encoding a IL-12 protein, wherein the protein is expressed and wherein an immune response is induced in a subject.

Yet another object of the invention is an immunogenic composition comprising a plasmid expressing the DNA sequence encoding an *O. tsutsugamushi* strain 110 kDa protein, wherein the protein is expressed and a plasmid expressing the DNA sequence encoding a GM-CSF protein, wherein the protein is expressed and wherein an immune response is induced in a subject.

Still another object of the invention the expression of the 110 kDa protein antigen in different host backgrounds of bacterial strains for use in different vaccine formulations against scrub typhus infection.

Yet still another object of the invention is a vaccine formulation comprising one or more polypeptide sequences of the 110 kDa protein of *O. tsutsugamushi* with or without adjuvant.

These and other objects, features and advantages of the present invention are described in or are apparent from the following detailed description of preferred embodiments.

BRIEF DESCRIPTION OF THE DRAWINGS

The invention will be described with reference to the drawings, in which like elements have been denoted throughout by like reference numerals. The representation in each of the figures is diagrammatic and no attempt is made to indicate actual scales or precise ratios. Proportional relationships are shown as approximations.

DETAILED DESCRIPTION

Figure 1:
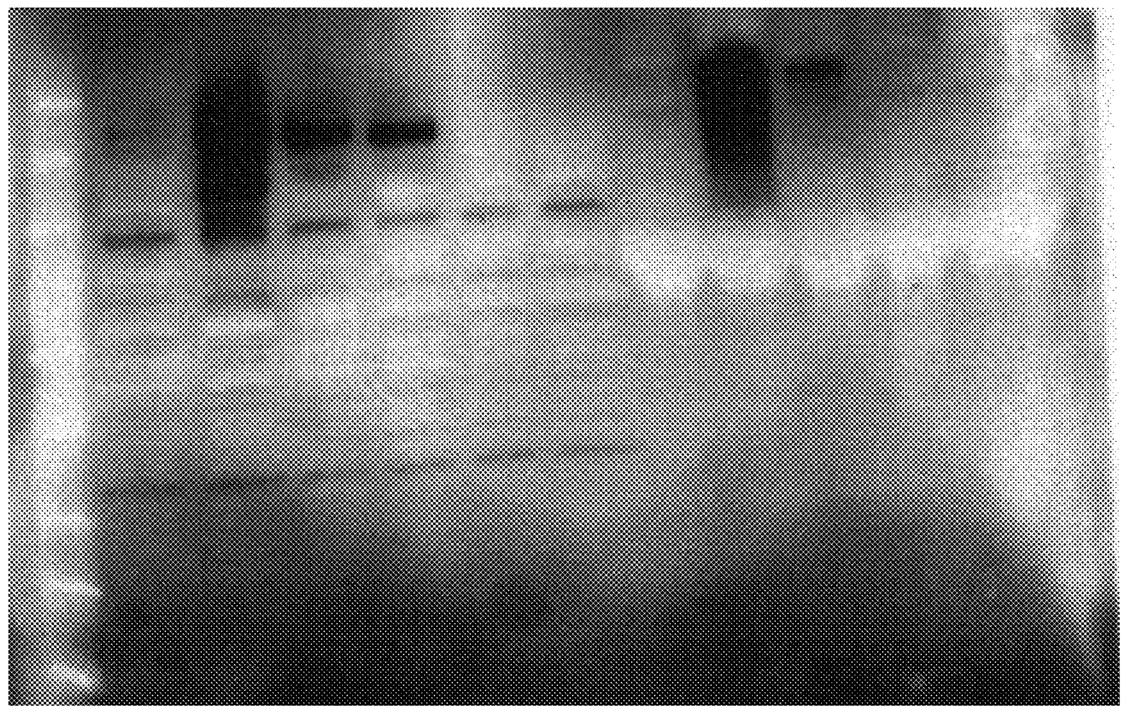
FIG. 1 shows the western blot confirmation of the expression of 110 kDa antigen from the *O. tsutsugamushi* strains Karp, Kato and Gilliam. Lane 1 is the molecular weight markers; lane 2 is the 110 kDa Kato strain protein inserted into VR 1020; lane 3 is the 110 kDa Karp strain protein inserted in VR 1020; lane 4 is the 110 kDa Gilliam strain protein inserted into VR 1020; lane 5 is the 110 kDa Gilliam strain inserted in VR 1012; lane 6 is VR 1020 alone; lane 7 is VR 1012 alone; lane 8 is the culture supernatant of 110 kDa Kato strain inserted into VR 1020; lane 9 is the culture supernatant of 110 kDa Karp strain inserted into VR 1020; lane 10 is the culture supernatant of 110 kDa Gilliam strain inserted into VR 1020; lane 11 is VR 1012 culture supernatant only; and lane 12 is VR 1020 culture supernatant only.

There are still no FDA licensed vaccines available for scrub typhus. Previous vaccine candidates require bacterial antigen that must be purified by extremely labor intensive methods after first propagating the organism in specialized laboratories (BSL-3). The short coming of non-living protein vaccines is that it can not produce specific CD8+ T-cells, which is required for cellular immunity. Both humoral and cellular responses are likely to be required for the protection against intracellular pathogens such as human immunodeficiency virus, *Mycobacterium tuberculosis, Leishmania major* and *Plasmodium yoelii*. Wolff et al has shown that direct intramuscular inoculation of plasmid or naked DNA encoding several reporter genes could induce protein expression within the muscle cells [11]. DNA vaccines mimic the effects of live attenuated vaccines in their ability to induce both humoral and cellular responses, including class 1 restricted CD8+ T-cell responses, while eliminating some of the safety concerns associated with live vaccines. DNA vaccines are relatively easy to produce and can be used for protective antigen discovery. We have successfully cloned the gene coding for the whole ORF of 110 kDa protein from the Karp strain of *O. tsutsugamusi* into a VR1020 plasmid as the DNA vaccine (Kp 110 DNA) (12, 13). The move toward using DNA vaccines has the potential to shorten the time necessary for developing and fielding an effective polyvalent vaccine against scrub typhus. This is especially important because of the extensive antigen diversity in the 110 kDa protein antigen found among the various strains of *O. tsutsugamushi*. Here we disclose recombinant constructs from the 110 kDa gene of *O. tsutsugamushi.*

EXAMPLE 1

Cloning and Expression of Recombinant 110 kDa Gene

The open reading frame (ORF) of the 110 kDa gene of *O. tsutsugamushi* was obtained by polymerase chain reaction (PCR) amplification. The forward primer, SEQ ID No. 1, comprised the 5' DNA sequence of 110 kDa ORF starting with the methionine initiation site but with an added kpn DNA restriction site at the 5' end. Similarly, the reverse primer containing the stop codon of the ORF, contained in SEQ ID No. 2, was designed with a Kpn I site at its 5' end. DNA template for the PCR reactions was obtained from DNA isolated from plaque-purified *O. tsutsugamushi* Karp strain grown in irradiated L929 cells [14]. The 110 kDa gene was amplified in a mixture of deoxynucleotide triphosphate, 1 mM of each primer, 1.5 U of TAQ™ polymerase (Perkin-Elmer, CA) in 10 mM TRIS™-HCl buffer, pH 8.3, 1.5 mM $MgCl^2$, and 50 mM KCl. The PCR reaction was started with 15 sec at 80° C., 4 min at 94° C., and followed by 30 cycles of 94° for 1 min, 57° C. for 2 min and 72° C. for 2 min. The last cycle was extended for 7 min at 72° C. Similar to the procedure used for the Karp strain, the ORF of the Kato and Gilliam strains was also amplified using the same forward primer as for Karp (SEQ ID No. 1) but reverse primers as in SEQ ID No. 3 for Kato and SEQ ID No. 4 for Gilliam. The sequence of the amplified Karp, Kato and Gilliam strain 110 kDa ORF is disclosed in SEQ ID No. 5, 6 and 7, respectively. When translated, these DNA sequences yield the amino acid sequence of SEQ ID No. 8, 9 and 10 for the Karp, Kato and Gilliam strains, respectively. Table 1 summarizes the sequences described.

The above amplified PCR product containing the kpn (BioLab, MA) and BamH I (Life Technology, MD) sites were ligated to kpn digested VR 1020 expression vector to yield VR 1020/Karp, VR 1020/Kato or a VR 1020/Giliam strain 110 kDa protein expression system. The VR 1020/110 protein expression systems for Karp, Kato and Gilliam are designated pKp110, pKato110 and pGm110, respectively. Although VR 1020 was utilized, any plasmid or viral expression system can be used as long as polypeptide is expressed.

Expression of the VR 1020/110 kDa expression systems are expressed in HEK 293 cell lines. Growing cultures of HEK 293 cell line containing these plasmids are then harvested and the cell culture fluid and cell lysate analyzed by western blotting using specific anti-110 kDa antiserum as a probe to evaluate expression of the 110 kDa ORF. As shown in FIG. 1, analysis of expressed product yields a full length 110 kDa moiety in both the culture fluid and cell lysate (FIG. 1).

TABLE 1

| SEQ ID No. | Description |
|---|---|
| SEQ ID No. 1 | Forward PCR primer pKp110 |
| SEQ ID No. 2 | Reverse PCR primer pKp110 |
| SEQ ID No. 3 | Reverse PCR primer pKato110 |
| SEQ ID No. 4 | Reverse PCR primer pGm110 |
| SEQ ID No. 5 | Karp 110 DNA sequence |
| SEQ ID No. 6 | Kato 110 DNA sequence |
| SEQ ID No. 7 | Gilliam 110 DNA sequence |
| SEQ ID No. 8 | Amino acid sequence Karp 110 |
| SEQ ID No. 9 | Amino acid sequence Kato 110 |
| SEQ ID No. 10 | Amino acid sequence Gilliam 110 |

Based on the above studies, the recombinant constructs can be utilized to induce a protective immune response in humans. The immunizing composition will be composed of:

a. a plasmid, such as VR 1020, containing the DNA sequence encoding the entire or a fragment of the *O. tsutsugamushi* 110 kDa protein, wherein said protein is expressed; and b. a plasmid, such as VR 1020, containing the DNA sequence encoding a cytokine adjuvant, wherein said cytokine adjuvant is expressed and wherein an immune response is induced. The cytokine adjuvant is either IL-12 or GM-CSF.

The DNA sequence inserted into the plasmid is either the entire or fragment of *O. tsutsugamushi* 110 kDa protein derived from one or more of the *O. tsutsugamushi* strains Karp, Kato and Gilliam. Furthermore, the sequence inserted is all or a portion of the DNA sequence of SEQ ID No. 5, 6 and 7 and which encodes the entire or a fragment of one or more of polypeptide sequences of SEQ ID No. 8, 9 and 10.

The method of inducing an immune response comprises the following steps:

a. administering a priming dose comprising 2–10 mg per dose each of one or more plasmids containing a DNA sequence encoding the entire or fragment of the110 kDa protein from one or more *O. tsutsugamuchi* strains selected from the group consisting of Karp, Kato and Gilliam, wherein said protein is expressed and a plasmid containing the DNA sequence encoding a cytokine adjuvant, wherein said cytokine adjuvant is expressed;

b. admininistering 1 to 4 boosting doses with the first boosting dose at least 1 week after said priming dose.

The boosting dose contains all or a fragement of one or more *O. tsutsugamuchi* DNA sequences SEQ ID No. 5, 6 and 7 encoding the Karp, Kato and Gilliam 110 kDa polypeptides SEQ ID No. 8, 9, and 10 from *O. tsutsugamuchi*. The boosting DNA sequence, however, is from the same strain as in the priming dose. The boosting dose also can include a plasmid expressing a DNA sequence encoding a cytokine adjuvant such as IL-12 or GM-CSF.

EXAMPLE 2

Use of Kp 110 DNA as a Vaccine Candidate in Mouse Model

The ability of the pKp110 to elicit a protective immune response, murine studies were conducted using these constructs as immunogen. Female Swiss outbred CD-1 mice (Charles River Laboratories, Wilmington, Mass.), 18–24 g, were used throughout the study. Mice were immunized intramuscularly with 28 g×½" needle at the two thighs 25 ul/site, total of 50 ul containing different amount of Karp 110DNA. Mice were challenged with the lethal dose of 1000×$LD_{50}$ of Karp in 0.2 ml of Snyder's 1 buffer four weeks after one immunization. Date of onset of disease and date of death were recorded for individual mice. The morbidity and mortality were monitored at least twice a day for 21 days post-challenge.

The protective efficacy of pKp 110 DNA against challenge in mouse model is summarized in Table 1 and Table 2. As shown in Table 1, pKp110 demonstrated a protective efficacy with IL-2 or GM-GSF that was significantly better than that of pKp56, which is the VR1012 expression vector containing the 56 kDa protein construct of *O. tsutsugamushi*. However, pKp 110 was equivalent but slightly less efficacious than pKp47, which is the VR 1020 vector containing the 47 kDa recombinant construct of *O. tsutsugamushi*. However, a likely advantage of using the 110 kDa construct verses the 47 kDa construct is because of the potential for induction of an autoimmune response by the 47 kDa immunogen. This possibility is predicated based on the homology of a large region of the 47 kDa DNA sequence (15) with the eukaryotic trypsin-like gene (16, 17).

TABLE 2

Protection of Mice immunized with pKarp110 using pIL-12 (10 ug) as adjuvant

| Immunogen | % Survival Exp 1($10^3$) | | Exp 2($10^5$) | | Exp 3($10^3$) | |
|---|---|---|---|---|---|---|
| 1. PBS (IL-12 only) | 1/12 | 8.3% | | | | |
| 2. p1012, 100 ug | 1/10 | 10% | 0/10 | 0% | 0/10 | 0% |
| 3. p1020, 100 ug | 1/9 | 11% | 1/10 | 10% | 1/10 | 10% |
| 4. pKp110 (no IL-12), 100 ug | | | 1/10 | 10% | 4/10 | 40% |
| 7. pKp56, 100 ug | 5/12 | 42% | 0/10 | 0% | 2/10 | 20% |
| 8. pKp56, 50 ug | | | 1/10 | 10% | 2/10 | 20% |
| 9. pKp47, 100 ug | 6/10 | 60% | 2/10 | 20% | 7/10 | 70% |
| 10. pKp47, 50 ug | | | 4/10 | 40% | 6/10 | 60% |
| 11. pKp110/pKp56, 50 ug each | 6/10 | 60% | 3/10 | 30% | 7/10 | 70% |
| 12. pKp110/pKp47, 50 ug each | | | 9/10 | 90% | 8/10 | 80% |

TABLE 3

Protection of Mice Immunized with pKarp110 using pGM-CSF (10 ug) as the adjuvant

| Immunogen | % Survival Exp 1 ($10^3$) | | Exp 2 ($10^5$) | | Exp 3 | |
|---|---|---|---|---|---|---|
| 1. PBS (GMCSF only) | 3/12 | 25% | | | | |
| 2. p1012, 100 ug | 0/12 | 0% | 0% | 0/10 | | |
| 3. p1020, 100 ug | 1/10 | 10% | 0% | 0/10 | | |
| 4. pKp110 (no GMCSF), 100 ug | | | | | | |
| 7. pKp56, 100 ug | 3/12 | 25% | 3/10 | 30% | | |
| 8. pKp56, 50 ug | | | 1/10 | 20% | | |
| 9. pKp47, 100 ug | 10/10 | 100% | 7/10 | 70% | | |
| 10. pKp47, 50 ug | | | 10/10 | 100% | | |
| 11. pKp110/pKp56, 50 ug each | 4/10 | 40% | 7/10 | 70% | | |
| 12. pKp110/pKp47, 50 ug each | | | 8/10 | 80% | 12/15 | 80% |
| 13. pKp110/pKp47, 25 ug each | | | | | 9/15 | 60% |

EXAMPLE 3

Antigen Reagent for Scrub Typhus Assays and Subunit Vaccines

The recombinant 110 kDa *O. tsutsugamushi* antigen, because of its immunoreactivity, has significant utility as a diagnostic antigen in immunoassays for scrub typhus. The recombinant antigen, because of its high-level of immunoreactivity to patient sera, is well suited as a standardized antigen for assays designed for the detection of prior infection by *O. Isutsugamushi* and diagnosis of scub typhus. Recombinant 110 kDa antigen can be incorporation into any antibody-based assay including enzyme-linked immunosorbent assays and rapid flow immunoassays. The antigens are easily recombinantly expressed using any expression system, including pET 24 and are thus capable of standardized production quality.

An example of an expression system for recombinant expression of *O. tsutsugamuchi* 110 kDa antigen is the construction of the pET 24d/*O. tsusugamuchi* vector is constructed by first introducing DNA encoding for the *O. tsutsugamuchi* 10 kDa protein into the pET 24d vector. An expression system encoding 110 kDa antigen can be constructed by inserting either DNA encoding the entire 110 kDa protein or fragements of the gene or DNA sequences encoding a portion of the 110 kDa gene. In this example, either *O. tsutsugamuchi* Karp, Kato or Gilliam strain DNA for fragment A, which encodes for Gly 140 to Asn 587 of the 110 kDa protein or fragment B, encoding for Val 507 to Asn 903 of the 110 kDa protein, is inserted into the pET24d vector. The DNA sequence of Karp, Kato and Gilliam strains fragment A is SEQ ID No. 11, 13 and 15 respectively. These sequences encode the Karp, Kato and Gilliam polypeptide sequences SEQ ID No. 17, 19, and 21, respectively. The DNA sequence for Karp, Kato and Gilliam strains for fragment B is SEQ ID No. 12, 14 and 16 which encodes for the Karp, Kato and Gilliam polypeptides sequences SEQ ID No.18, 20 an 22, respectively. The *O. tsutsugamuchi* fragment and its associated SEQ ID numbers are summarized in Table 4.

Each of the recombinant *O. tsutsugamuchi* 110 kDa polypeptides are similarly constructed. For example, the fragments A or B of the Karp strain is produced by amplifying the fragment from native DNA with PLATINUM Taq DNA POLYMERASE HIGH FIDELITY® (Invitrogen, Carlsbad, Calif.) using genomic DNA of *O. tsutsugamuchi* karp strain as template. The forward primer for fragment A was SEQ ID number 23 and the reverse primer was SEQ ID No. 24. The resulting PCR product was then inserted between the NcoI and EcoRI sites of the pET24d plasmid. The resulting plasmid pET24d-110A Karp encodes the A fragment (Gly-140 to Asn-587). For fragment B, the forward and reverse PCR primers were SEQ ID No. 25 and 26, respectively. The fragment B (Val-507 to Asn-903) sequence was inserted into pET24d as for fragment A. The sequence of both constructed plasmids (pET24d-110A Karp and pET24d- 110B Karp) was verified by sequencing.

The pET 24 vectors containing the 110 kDa fragment A and B proteins were expressed in *E. coli* BL21(DE3) bacteria. Cells were grown in L-broth containing 50 μg/ml kanamycin at 37° C. to an $O.D._{600}$ 0.8 at which time 1PTG (1 mM) was added. The culture was then incubated with shaking for 4 hrs at 37° C. Cells were harvested and weighted (about 5.5 g of wet cells per liter culture). The cell pellets were re-suspended in 7 volume of buffer A (20 mM Tris-HCI, pH 8.0, 5 mM EDTA), and lysed. The cell lysate was cleared by first centrifugation at 6,000 rpm (IEC MultiRF rotor) for 10 min then a second centrifugation at 9,600 rpm (the same rotor) for 30 min. The 110 kDa antigen fragments were then precipitated by adding solid ammoninm sulfate to the lysate to 30% saturation (0.164 g/ml) for fragment A and 40% saturation (0.226 g/ml) for fragment B. After centrifugation at 9,600 rpm for 30 min at 4° C., the protein pellet was re-suspended with one-seventh volume of buffer A. Subsequent to resuspension in Tris buffer, fractions A and B were purified through a gel filtration column (ZORBAX Bio Series GF-450™, Agilent Technology, Palo Alto, Calif.).

The *O. tsutsugamushi* peptides can be utilized either alone or in combinantion with other *O. tsutsugamushi* fragment antigens in immunodiagnostic assays comprising the following steps:

1. Microtiter plates with 96 wells were coated with 0.3 μg/well of any or all of the recombinant proteins represented by SEQ ID No. 17–22 and stored in 4° C. for 2 days.
2. Plates are washed ×3 with wash buffer (0.1% TWEEN-20 in PBS).
3. Plates are blocked with 200 μl/well of blocking buffer (5% skim milk in wash buffer) for 45 minutes and then rinsed three times.
4. Sera is diluted in blocking buffer and 100 μl/well is added and incubated for 1 to 2 hours.
5. Plates are washed three times with wash buffer.
6. Plates are then incubated with 100 μl/well of enzyme-labeled (e.g. peroxidase) anti-human immunoglobulin for 1 hour.
7. The plates are washed three times with wash buffer.
8. Substrate is added to the wells and read after 15 to 30 minutes.

A standard curve is constructed by conducting the above ELISA procedures with the recombinant proteins but utilizing a range of concentrations of specific antibody to *O. tsutsugamuchi*. The extent of measured binding of patient serum antibody is compared to a graphic representation of the binding of the *O. tsutsugamuchi*-specific antibody concentrations.

Sensitivity of antibody-based assays, such as ELISA, can be enhanced by substituting the enzyme-substrate step with a molecular detection method. An example of a molecular method employed is the amplification of circular DNA by rolling circle amplification (RCA). In RCA, antibody specific to *O. tsutsugamuchi* is conjugated with a single stranded DNA primer comprising the following steps:

a. 1 mg of sulfo-GMBS powder was added to 4 mg of antibody $F(ab')_2$ in 1 ml, in the dark, for 30 minutes at 37° C., followed by 30 minutes at room temperature;
b. 2 ml of phosphate buffered saline (PBS) was added to the reaction mixture from a;
c. the reaction mixture in b, above, was applied unto a preequilibrated Presto Desalting Column® (Pierce Biotechnology, Inc, Rockford, Ill.);
d. the applied material was eluted with PBS and the eluted fractions monitored by absorbance at 280 nm;
e. pooled fractions containing maleimide-acitivated antibody was concentrated and stored at 4° C. in the dark until used;
f. activated DNA was prepared by res-suspending 0.44 mg of thio-DNA (C6 S-S®) (MWG-Biotech Inc, High Point, N.C.) in 150 μl TE buffer with 15 μl of 1 M DTT and incubated at room temperature for 30 minutes;
g. the DTT was removed from the mixture of step g by applying the mixture to a G-50 micro column and spinning the column at 735× g for 2 minutes;
h. the activated antibody and activated thio-DNA was then mixed and the mixture incubated in the dark at room temperature for 1 hour then overnight at 4° C.;
i. product from step h was analyzed by gel electrophoresis.

RCA reactions were undertaken the method comprising the following steps:

a. mix together on ice 5 nM of primer-conjugated antibody, 10 nM circular DNA, 200 ng of *E. coli*, single-stranded DNA binding protein (SSB), 13 units of T7 SEQUENASE™ and 0.4 mM each of dATP, dCTP, dGTP, 0.3 mM dTTP and 0.1 mM FITC-dUTP in 25 μl of reaction buffer at pH 7.9 containing 20 mM TRIS™-acetate, 10 mM magnesium acetate, 50 mM potassium acetate and 1 mM DTT;
b. incubate the mixture of step at 37° C. for up to 30 minutes;
c. RCA products are then analyzed analyze the products by measuring fluorescence incorporation of DNA product.

As alternative to RCA, PCR can be utilized using a primer complimentary to the antibody-conjugated DNA, made as described for RCA. Amplification is conducted by utilizing a DNA primer complementary to a template sequence contained on the conjugated DNA.

In addition to immunoassays, the recombinant amino acid sequences can be utilized to induce an immune response, as in a vaccines against *O. tsutsugamushi* infection. A prophetic example of the use of the amino acid sequences comprises the following steps:

a. administering a priming dose comprising 50 μg to 2 mg per dose of one or more of the entire or fragment of a recombinant polypeptide encoded an amino acid sequence selected from the group consisting of SEQ ID No. 8, 9 and 10; and
b. administering 1 to 4 boosting doses with the first boosting dose at least 1 week after priming dose comprising 50 μg to 2 mg per dose of one or more of the entire or fragment of a recombinant polypeptide encoded by an amino acid sequence selected from the group consisting of SEQ ID No. 8, 9, and 10, wherein an immune response is elicited.

In the above example for inducing an immune response, a cytokine adjuvant can be included either in the administration of the priming or boosting doses or upon both the priming and boosting administrations of the polypeptides. The cytokine adjuvant can be any cytokine including IL-12 or GM-CSF.

TABLE 4

| SEQ ID No. | Description |
|---|---|
| SEQ ID No. 11 | DNA fragment A Karp strain |
| SEQ ID No. 12 | DNA fragment B Karp strain |
| SEQ ID No. 13 | DNA fragment A Kato strain |
| SEQ ID No. 14 | DNA fragment B Kato strain |
| SEQ ID No. 15 | DNA fragment A Gilliam strain |
| SEQ ID No. 16 | DNA fragment B Gilliam strain |
| SEQ ID No. 17 | Amino acid sequence fragment A Karp strain |
| SEQ ID No. 18 | Amino acid sequence fragment B Karp strain |
| SEQ ID No. 19 | Amino acid sequence fragment A Kato strain |
| SEQ ID No. 20 | Amino acid sequence fragment B Kato strain |
| SEQ ID No. 21 | Amino acid sequence fragment A Gilliam strain |
| SEQ ID No. 22 | Amino acid sequence fragment B Gilliam strain |

REFERENCES

1. Brown, G. W., D. M. Robinson, D. L. Huxsoll, T. S. Ng, K. J. Lim, and G. Sannasey. 1976. Scrub typhus: a common cause of illness in indigenous populations. Trans. R. Soc. Trop. Med. Hyg. 70:444–448.
2. Brown, G. W., J. P. Saunders, S. Singh, D. L. Huxsoll, and A. Shirai. 1978. Single dose doxycycline therapy for scrub typhus. Trans. R. Soc. Trop. Med. Hyg. 72:412–416.
3. Watt G, C. Chouriyagune, R. Ruangweerayud, P. Watcharapichat, D. Phulsuksombati, K. Jongsakul, P. Teja-Isavadham, K. Bhodhidatta, K. D. Corcoran, G. A. Dasch, D. Stickman. 1996. Scrub typhus poorly responsive to antibiotics in northern Thailand. Lancet 348:86–89.
4. Watt G, P. Kantipong, K. Jongsakul, P. Watcharapichat, D. Phulsuksombati, D. Strickman. 2000. Doxycycline and rifampicin for mild scrub-typhus infections in northern Thailand: a randomised trial. Lancet 356:1057–1061.
5. Mathai E, J. M. Rolain, G. M. Verghese, O. C. Abraham, D. Mathai, M. Mathai, D. Raoult. 2000. Out break of scrub typhus in southern India during the cooler months. Ann. New York Acadamy 990: 359–364.
6. Smadel, J. E., H. L. Ley, Jr., F. H. Diercks, R. Traub, V. J. Tipton, and L. P. Frick. 1951. Immunization against scrub typhus. I. Combined living vaccine and chemoprophylaxis in volunteers. Am.J.Hyg. 53:317–325.
7. Smadel, J. E., H. L. Ley, Jr., F. H. Diercks, P. Y. Paterson, C. L. Wisseman, Jr., and R. Traub. 1952. Immunization against scrub typhus: duration of immunity in volunteers following combined living vaccine and chemoprophylaxis. Am.J.Trop.Med.Hyg. 1:87–99.
8. Eisenberg, G. H., Jr., and J. V. Osterman. 1979. Gamma-irradiated scrub typhus immunogens: broad-spectrum immunity with combinations of rickettsial strains. Infect. Immun. 26:131–136.
9. Eisenberg, G. H., Jr., and J. V. Osterman. 1978 Effects of temperature on the stability of Rickettsia tsutsugamushi and Gamma-irradiated scrub typhus immunogens. Infect. Immun. 22:298–300
10. Ohashi, N., A. Tamura, H. Sakurai, and T. Suto. 1988. Immunoblotting analysis of anti-rickettsial antibodies produced in patients of tsutsugamushi disease. Microbiol. Immunol. 32:1085–1092
11. Wolff J A, Malone R W, Williams P, Chong W, Acsadi G, Jani A, Felgner P L. 1990. Direct gene transfer into mouse muscle in vivo. Science 247:1465–68.
12. Hoffman, S. L., D. L. Doolan, M. Sedegah, J. C. Aguiar, R. Wang, A. Malik, R. A. Gamizinski, W. R. Weiss, P. Hobart, J. A. Norman, M. Margalith and R. C. Hedstrom. 1997. Strategy for development of a pre-erythrocytic *Plasmodium falciparum* DNA vaccine for human use. Vaccine (15): 842–845.
13. Coker, C. M. Majid and S. Radulovic. 2003. Development of *Rickettsia prowazekii* DNA vaccine. Annals of N.Y. Acad. of Sci. 990:757–764.
14. Kelly, D. J., G. A. Dasch, T. C. Chye, and T. M. Ho. 1994. Detection and characterization of *Rickettsia tsutsugamushi* (Rickettsiales: Rickettsiaceae) in infected *Leptotrombidium* (*Leptotrombidium*)*fletcheri* chiggers (Acari: Trombiculidae) with the polymerase chain reaction. J. Med. Entomol. 31:691–699.
15. Kim, I. J., I. S. Kim, I. H. Choi, W. H. Chang and M. S. Choi. 1994. Characterization of gene for 47 kDa protein of *Rickettsia tsutsugamushi*. GENEBANK Accession AAA26374 (19-04-1994).
16. Walsh, K. A., and H. Neurath. 1964. Trypsinogen and chymotrypsinogen as homologous proteins. Proc. Natl. Acad. Sci. (USA) 52:884.
17. Zumbrunn, J., and B. Trueb. 1996. Primary structure of a putative serine protease specific for IGF-binding proeins. FEBS Lett. 398:187–192.

Obviously, many modifications and variations of the present invention are possible in light of the above teachings. It is therefore to be understood that, within the scope of the appended claims, the invention may be practiced otherwise than as specifically described.

We claim:

1. An isolated recombinant 110 kDa polypeptide of *Orientia tsutsugamushi* or an antigenic fragment thereof, wherein the recombinant polypeptide consists of the amino acid sequence selected from the group consisting of SEQ ID NO: 8, SEQ ID NO: 9 and SEQ ID NO: 10.

2. The recombinant polypeptide of claim 1, wherein the polypeptide is of *Orientia tsutsugamushi* strain Karp, Kato, or Gilliam.

3. The recombinant polypeptide of claim 1, wherein the polypeptide is encoded by a DNA sequence selected from the group consisting of SEQ ID NO: 5, SEQ ID NO: 6 and SEQ ID NO: 7.

4. The recombinant polypeptide of claim 3, wherein said DNA encoding the polypeptide is inserted in pET24 plasmid.

5. A diagnostic antigen comprising the isolated recombinant polypeptide of claim 1, or said antigenic fragment.

6. A method of inducing an immune response against *Orientia tsutsugamushi* in a subject comprising (a) administering to said subject a priming dose comprising 50 μg to 2 mg per dose of the recombinant polypeptide of claim 1 or said antigenic fragment; and (b) administering 1 to 4 boosting doses comprising 50 μg to 2 mg per dose of said recombinant polypeptide or said antigenic fragment at least one week after the priming dose, thereby inducing the immune response.

7. The method of claim 6, wherein said priming dose includes a cytokine adjuvant selected from the group consisting of IL-12 and GM-CSF.

8. The method of claim 6, wherein said boosting dose includes a cytokine adjuvant selected from the group consisting of IL-12 and GM-CSF.

* * * * *

SEQUENCE LISTING

```
<160> NUMBER OF SEQ ID NOS: 26

<210> SEQ ID NO 1
<211> LENGTH: 23
<212> TYPE: DNA
<213> ORGANISM: Orientia tsutugamushi

<400> SEQUENCE: 1

ggggtaccat ggctccagac aat                                    23
```

-continued

```
<210> SEQ ID NO 2
<211> LENGTH: 23
<212> TYPE: DNA
<213> ORGANISM: Orientia tsutugamushi

<400> SEQUENCE: 2

ggggatccct accctatacc ttt                                              23


<210> SEQ ID NO 3
<211> LENGTH: 23
<212> TYPE: DNA
<213> ORGANISM: Orientia tsutugamushi

<400> SEQUENCE: 3

ggggatccct accctatacc ttt                                              23


<210> SEQ ID NO 4
<211> LENGTH: 23
<212> TYPE: DNA
<213> ORGANISM: Orientia tsutugamushi

<400> SEQUENCE: 4

ggggatccct accctatacc ttt                                              23


<210> SEQ ID NO 5
<211> LENGTH: 2742
<212> TYPE: DNA
<213> ORGANISM: Orientia tsutugamushi

<400> SEQUENCE: 5

atggctccag acaataaacc aattaacaac aaatcttcag acttaatatc aaaatcacaa      60

gagcaaaata ttaaagatct tggcaagaaa atagatttaa tgatacaaca agttgatact     120

cttgatagta aaatacgatc aaggtcagca gaaggcaatg cactaaatgt tgaagtaatt     180

agagcattaa ataatgtaat gaagaatgtg acagagacgc tacaacaatt ctcgcaagaa     240

atacttcaac aatctaaact agcacgtcaa caacctcaaa aaggtccata taatgatgcc     300

tttcgtaaga aaagagctga ggctaaagaa aaaaaagcac accttgaaaa gcaaaagcaa     360

gaattcatgg ggttagtatc taaattaggc gaggaaatga agctagtagg caaaccaggt     420

ggacagatgt ctgagataaa agatactcta gataagcttt atgcaatagt taacaagtca     480

gcacagcatc aactgcaaaa aactcttggt gagcttcagg caatgattaa tgaacataaa     540

cagaaccagc tacaagatgc tctagacgat ctggaaaata taatcaacga tcataaacag     600

aatcaaaaag aacagaaggc tcctatttca cctgaaacac atgcacataa tgtaacgtct     660

attaaaaacc aagctcaaca aaatgctggt attaatcaac cggatgcacc taaatctgct     720

agcaaatcag cagcagatat atcacaatct actcagaatt cttctccagc gacaccaact     780

ggcacagggc aacaacaaga gccacaaaaa acgcctcctc ctgttccacc taaacctagt     840

aaaaatacaa tagaggaatt aaaggctaaa atagctcaag ctcaacaaaa tgctggtatt     900

aatcaaccag gtgcacctaa atctgctagc aaaccagcag cagatatacc acaatctact     960

cagcattctt ctccagcaac atcaactggc acagggcaac aacaagagcc acaaaaaaca    1020

cctcctcctg ttccgcccaa acctagtaaa gatacaatag aggaattaaa ggctaaaata    1080

gctcaagctc aacaaaatgc tggtattaat caaccagatg cgcctaaatc tgctagcaaa    1140

tcagcagaag atatattaca atctactcag cattcttctc cagtaacacc aactgctaca    1200
```

-continued

```
gcacaacaac atgagccaca aaaaacacct cctcctgttc cacctaaacc tagtaaaaat   1260

ataatcgaag aattaaaagc taagatatca caaactcaac aacaggttga ccggcaatca   1320

tatattaatc caagtagtag tccccaacct cttagttcaa ctatagagca tgctaaagac   1380

agagtattaa cattagatcc acaatataga cacgctcaag ctgctcaaaa tatgagtgga   1440

ccagatgctg aaacaaatca gaagccagta gatccaattc tacaggcatt taaagattta   1500

aaagctctaa taaatagcgt gattgctgga gatgatagtt tcaaaatatg gcaacagcaa   1560

aatccaagca aaaatctaga tgattttaaa cataatccaa cgcaaatgga tagcttatct   1620

caagagacta aagagttact atctagcctt ggatctgaag gatatgctaa tattatgggt   1680

tcagcagcaa atattgatcc agctcagcaa atgtcatttg ctgtatcttt tagtacatta   1740

gattggggga gtcaggctaa ttctgttggc aatactattc aaaaaactat taccaatgat   1800

gctggtgaaa aagttacaga ccttataagc catatgcata aaactcagct cagtgctaat   1860

gttaatggtg ttacaaaaac tgttactaaa caccgtacca tagatattcc aagggcagtt   1920

gaagaaaaca aaggaccttt agatcttgcc ttagtagcac aagatgcaac aggaaaaaat   1980

atgtctgagt caaaagcagt gtatctaact gctcattata accaagaagg gaaattagta   2040

gaaattactc atccggaacc gatgctattt tttagtgatg agcctagctc tccagcttat   2100

acagttataa ataatgaagt ttatactttg ccaattacta gagaaaaata tgaccagcta   2160

accaaagaaa tatcacaaaa tatacaggaa caagacaaag ataaagagag agaacaggaa   2220

gctgtggata agtttacagt gggttctcgt caaactgata ttcataacga aaaaagtatt   2280

caacatgctg atgaagtaag taaggatgct cctaaatctt taaaatctat tgctcatgat   2340

gaaaacaaaa ataaaattca aggcactgat cataaatcga aaaacagcaa tgaatatgtt   2400

caacatatga ttaactcgtt taatcaaaac tataacaaaa ttgattctaa cgagccaaat   2460

cgtactgaac aggtaaaact gaagcctgta gtcaaatcaa taccagaatc tccaaaaaac   2520

tctactcaga ttgatcctaa tgaagaaggt agtattggat acgtaaaacg tgtaattgaa   2580

tcaatggaac aaacatcacc aaatcctagt gaaatagcac aaagattaca ggtaaatcta   2640

gctaatagtt ctcagcgtag ttctagtatg tctattaata ctcctactaa tactcctcgc   2700

aataataacc aaagcaaatc tcagacaaaa ggtataggtt ag                      2742
```

```
<210> SEQ ID NO 6
<211> LENGTH: 2850
<212> TYPE: DNA
<213> ORGANISM: Orientia tsutugamushi

<400> SEQUENCE: 6

atggctccag acaataaacc aattaacaac aaatcttcag gcttaatatc aaaatcacaa     60

gagcaaaata ttaaagatct tggcaagaaa atagatttaa tgatacaaca agttgatact    120

cttgatagta aaatgcgatc aaggtcagca gaaggtaata cactagatgt taaagtaatt    180

agagcattaa ataatgtaat gaagagtgtg ccagagacgc tacaacaatt ctcgcaagaa    240

atacttcaac aatctaaact agcacgtcaa caacctcaaa acggtcaata taatgatgct    300

tttcgtaaga aaagagctga ggcaaaagaa aaaaaagaac gccttgaaaa gcaaaagcaa    360

gaattcatgg ggttagtatc taaattaggc gaggaaatga agctagtagg caaaccaggt    420

ggacagatat ctgagataaa agatactatt gataagcttc atgcaatagt taacaagtca    480

gcacagcatc aactgcaaaa aactcttggt gagcttcagg caatgattaa tgaacataaa    540

cagaaccagc tacaagatgc tctagatgat ctggaaaata taatcaacga tcataaacag    600
```

-continued

```
aatcaaaaag aacagaagtc tactattcca cctgaaaaac atacacatga tgtaacatct    660
attaaaaacc aagctcaaca aaatactggt attactcaac cagatgcacc taaatctgct    720
agcaaatcag cagcagatat atcacaatct cctcagcgtt cttctccagc aacgccaact    780
agcaaatcag cagcagatat atcacaatct cctcagcgtt cttctccagc aacgccaact    840
aaaaatacaa tcgaagctat aaatgctaaa atagctcaag ctcaacaaaa tgctggtatt    900
aatcaaccag atatagctaa atctgctagc aaatcagcag cagatatacc acaatctcct    960
cagcattctt ctccagtaac accaactgct acagtgcaac aacacgagcc acaaaaaacg   1020
actcctcctg ttccacctaa acctagtaaa aatataatcg aagaattaaa tgctaaaata   1080
gctcaagctc aacaaaatgc tggtattaat caaccagatg cacctaaatc tgctagcaaa   1140
tcagcagaag atatatcaca atctactcag cattcttctc cagtaacacc aactgctaca   1200
gcacaacaac atgagccaca aaaaacacct cctcctgttc cacctaaacc tagtaaaaat   1260
ataatcgaag aattaaaagc taagatatca caaactcaac aacaggttaa tcagcaatca   1320
tatattaatc caagtagtag tcccaaacct cttagttcaa ctatagagca tgctaaagac   1380
agagtattaa tatcagatcc acaatataga catgctcaag ctgctcaaaa tatgagtgga   1440
ccagaggctg aaacaaatca gatgccagta gatcaaattc tacaagcatt taaagattta   1500
aaagcactta taaatagtgt gattgctgaa gatgataagt ttaaagtatg gcaacagcaa   1560
aatcaaagca aaagcctaga tgattttaaa cgtgatacaa cacaaatgga tagcttatct   1620
caagagacta aagagttact atctagcatc ggatctgcag gatatgctaa cattatgggc   1680
tcaacagcaa atattgaaca agctcagcaa atgtcatttg ctgcatcttt tagtacatta   1740
gattgggcta ctcatgctaa ttctgttggc aatactactc aaaaaactat taccaatgat   1800
gctggtgaaa aagttacaga ccttataagc catagccata aaactcagct cagtgctagt   1860
gttaatggtg ttacaaaaac tgttactaaa caccgtacca tagatattcc aagggcagtt   1920
gaaaaaaaca aaggaccttt agatcttgct ttagtagcac aagatgaaac tggaaaaaat   1980
atgtctgagt caaaagcagt gtatctaact gctcattata accaagaagg aaaattagta   2040
gaaatgactc atcctgaacc tctgagattc tttagtgatg agcctggctc tccagcttat   2100
acagttataa ataatgaagt ttatactttg ccaattacta aagaaaaata tgaacagcta   2160
accaaagaaa tatcacaaaa tatacaggaa caggataaag ataaagacat agaacaggaa   2220
gctatggata agtttacagt aggttctcgt caaactgata ttcataaaga aaaaagtatt   2280
caacaggctg atgaagtaag tactgatgag cctaaatcct taaagtctat gaatgagttt   2340
acaatagcct ctcgtcaaac tgatgatatc tataacgaga aaagtactcg aaatcctgaa   2400
gaaataagta gcgatgctcc taaatcttta aaatctattg ctcctgatga aaacaaaaat   2460
aaaattcaaa gcactgatca taaatcgaaa aacagcaatg aatatgttca acatatgatt   2520
aactcgttta atcaaaacta taacaaaatt gattctaacg aaccaaatcg tactgaacag   2580
gtaaaactga agcctgtagt caaatcaata ccagaatctc caaaaaactc tactcagatt   2640
gatcctaatg atgaaggtag tattggatat gtaaaacgtg tagttaaatc aatggaacaa   2700
acatcaccaa gtcctagtga gatagcacaa agattgcagt taaatctagc taatagttct   2760
cagcgtagtt ctagtatgtc tattaatact cctactaata ctcctcgcaa taataaccaa   2820
agcaaatctc agacaaaagg tatagggtag                                    2850
```

<210> SEQ ID NO 7

-continued

<211> LENGTH: 2862
<212> TYPE: DNA
<213> ORGANISM: Orientia tsutugamushi

<400> SEQUENCE: 7

```
atggctccag acaataaacc aattaacaca aaatcttcag gcttaatatc aaaatcacaa     60
gagcaaaata ttaaagatct tggcaagaaa atagatttaa tgatacaaca aattgatact    120
cttgatagta aaatgcgatc aaggtcagca gaaggcagtg cactaaatgt taaagtaatt    180
agagcattaa ataatgtaat gaagaatgtg ccagagacgc tacaacaatt ctcgcaagaa    240
atacttcaac aatctaaact agcacgtcaa caaccgcaaa aaggtcaata taatgatgcc    300
tttcgtaaga aaagagctga ggctaaagaa aaaaagggac accttgaaaa gcaaaagaaa    360
gaattcatgg ggttagtatc taaattaggc gaggaaatga agctagtagg caaatcaggt    420
ggacagatgt ctgagataaa agatactcta ggtaagcttc aagcaataat taataagcag    480
acccaacagc aactacaaaa tactctgact gatctacaga aaataattaa tgaacacaaa    540
cagagccagc tacaagaggc tctagatgat ctggaaaata taatcaacga tcataaacag    600
aatcaaaaag aacagaaggc ccctattcca cctgaaaaac atgcacatga tgtaacacct    660
attaaaaatc aagctcaaca aaatgctggt attaaccaac cagatgcacc taagtctgct    720
agcaaatcag cagcagatat atcacaatct actcagcatt cttcttcgtc tacaccaact    780
gctacagcgc aacaacaaga gccacaaaaa acgcctcctc ctgttccacc taaacctaat    840
aaaaatacaa tagaggaatt aaaggctaga gtagctcaag cccaacaaaa tgctggtatt    900
agtcaaccag atgcgcctaa atctgctagc aaatcagcag caggtatatc acaatctact    960
cagcattctt cttcgtctac accaactgct acagtgcaac aacaagagca aaaaaaaacg   1020
cctcctcctg ttccgcctaa acctagtaaa gatacaatcg aaactataaa agctaaagta   1080
gctcaagctc aacaaaatgc tggtattagt caaccagata cacctaaatc tgctagcaaa   1140
tcagcagcag atatatcaca gtctactcag aattcttctc cagtaacacc aactgctaca   1200
gtgcaacaac aagagcaaaa aaaaacgcct cctcctgttc cacctaaacc tagtaaaaat   1260
ataatcgaag aattaaaagc taagatatca caaactcaac aacatgttaa tcagcaatca   1320
tatattaatc caagtagtag tccacaacct cttagttcga ctatagagca tgctaaagac   1380
agagtattaa cattagatcc acaacataga caagcgcaag ctgcccaaac tgcccaagct   1440
atgagtggac cagatgctga aacaaatcag atgccagtag atccaattct acaagcattt   1500
aaagatttaa aagcgcttat aaatagtgta attgctgaag ataataagtt taaggcatgg   1560
caacagcaaa atccaagcaa aagtctagat gattttaaac atgattcaac gcaaatggat   1620
agcttatctc aagagactaa agagttacta tctagccttg gatacgaagg atatgctaac   1680
attatgggtt cagcagcaaa tattgattca gctcagcaaa tgtcatttgc tgcatctttt   1740
agtacattag attgggatac tcaagctaat tctgttggca atactgctca aaaaactatt   1800
accaatgagg ctggtgaaaa agttacagaa ctcgtaagcc acagtaataa agttcagctt   1860
agtgctagtg ttaatggcgt tacaaaaact gtcactaaac accgtactat agatattcca   1920
agtgcagtta aagaaaacaa aggacccttta gatcttgcct tagtagcaca agatgcaact   1980
ggaaaaaata tgcctgagtc aaaagcagta tatctaactg ctcattataa ccaagaagga   2040
aaattagtag aaatgactca tccggaacct ctgagattct ttagtgatga gcctagctct   2100
ccagcttata cagttataaa taatgaagtt tatactttgc caattactag agaaaaatat   2160
gaccagctaa ccaaagaaat atcacaaaat atacaggaac aagataaaga taaagagaga   2220
```

-continued

```
gaacaggaag ctgtggataa gtttacagta gggtctcgtc aaactgatat tcataaagaa   2280

aaaagtattc aacaggctga tgaagtaagt aacgatgctc ctaaatcctt aaagtctatg   2340

aatgagttta caataggctc tcgtcaaact tgcgatatct atcaagaaaa aagcactcaa   2400

gaaattgata aaataagtag cgatgatcct aaatctttaa agtctattgc tcctgatgaa   2460

aaccaaaaca aaattcaaag ccgacctgat tataaattgc aaaacagcaa tgaatatgtt   2520

caacatatga ttaaatcact tgatcaaaac tatcacaaaa ttgattctaa caaacaaaat   2580

tgtactgaac aggtaaaact gaagcctgta gtcaaatcaa tgccagaatc tccaaaaaac   2640

tctactcaga ttgatcctaa tgaggaaggt agtattggat atgtaaaacg tgtagttgaa   2700

tcaatggaac aaacatcacc aaatcctagt gagatagcac aaagattgca gttaaatcta   2760

gctaatagtt ctcagcatag ttctagtaca tctattacta ctcctactaa tactcctcgc   2820

aataataacc aaagcaaatc tcagacaaaa ggtataggt ag                      2862


<210> SEQ ID NO 8
<211> LENGTH: 913
<212> TYPE: PRT
<213> ORGANISM: Orientia tsutugamushi

<400> SEQUENCE: 8

Met Ala Pro Asp Asn Lys Pro Ile Asn Asn Lys Ser Ser Asp Leu Ile
1               5                   10                  15

Ser Lys Ser Gln Glu Gln Asn Ile Lys Asp Leu Gly Lys Lys Ile Asp
            20                  25                  30

Leu Met Ile Gln Gln Val Asp Thr Leu Asp Ser Lys Ile Arg Ser Arg
        35                  40                  45

Ser Ala Glu Gly Asn Ala Leu Asn Val Glu Val Ile Arg Ala Leu Asn
    50                  55                  60

Asn Val Met Lys Asn Val Thr Glu Thr Leu Gln Gln Phe Ser Gln Glu
65                  70                  75                  80

Ile Leu Gln Gln Ser Lys Leu Ala Arg Gln Gln Pro Gln Lys Gly Pro
                85                  90                  95

Tyr Asn Asp Ala Phe Arg Lys Lys Arg Ala Glu Ala Lys Glu Lys Lys
            100                 105                 110

Ala His Leu Glu Lys Gln Lys Gln Glu Phe Met Gly Leu Val Ser Lys
        115                 120                 125

Leu Gly Glu Glu Met Lys Leu Val Gly Lys Pro Gly Gly Gln Met Ser
    130                 135                 140

Glu Ile Lys Asp Thr Leu Asp Lys Leu Tyr Ala Ile Val Asn Lys Ser
145                 150                 155                 160

Ala Gln His Gln Leu Gln Lys Thr Leu Gly Glu Leu Gln Ala Met Ile
                165                 170                 175

Asn Glu His Lys Gln Asn Gln Leu Gln Asp Ala Leu Asp Asp Leu Glu
            180                 185                 190

Asn Ile Ile Asn Asp His Lys Gln Asn Gln Lys Glu Gln Lys Ala Pro
        195                 200                 205

Ile Ser Pro Glu Thr His Ala His Asn Val Thr Ser Ile Lys Asn Gln
    210                 215                 220

Ala Gln Gln Asn Ala Gly Ile Asn Gln Pro Asp Ala Pro Lys Ser Ala
225                 230                 235                 240

Ser Lys Ser Ala Ala Asp Ile Ser Gln Ser Thr Gln Asn Ser Ser Pro
                245                 250                 255
```

-continued

```
Ala Thr Pro Thr Gly Thr Gly Gln Gln Gln Glu Pro Gln Lys Thr Pro
            260                 265                 270

Pro Pro Val Pro Pro Lys Pro Ser Lys Asn Thr Ile Glu Glu Leu Lys
        275                 280                 285

Ala Lys Ile Ala Gln Ala Gln Gln Asn Ala Gly Ile Asn Gln Pro Gly
    290                 295                 300

Ala Pro Lys Ser Ala Ser Lys Pro Ala Ala Asp Ile Pro Gln Ser Thr
305                 310                 315                 320

Gln His Ser Ser Pro Ala Thr Ser Thr Gly Thr Gly Gln Gln Gln Glu
                325                 330                 335

Pro Gln Lys Thr Pro Pro Pro Val Pro Pro Lys Pro Ser Lys Asp Thr
            340                 345                 350

Ile Glu Glu Leu Lys Ala Lys Ile Ala Gln Ala Gln Gln Asn Ala Gly
        355                 360                 365

Ile Asn Gln Pro Asp Ala Pro Lys Ser Ala Ser Lys Ser Ala Glu Asp
    370                 375                 380

Ile Leu Gln Ser Thr Gln His Ser Ser Pro Val Thr Pro Thr Ala Thr
385                 390                 395                 400

Ala Gln Gln His Glu Pro Gln Lys Thr Pro Pro Pro Val Pro Pro Lys
                405                 410                 415

Pro Ser Lys Asn Ile Ile Glu Glu Leu Lys Ala Lys Ile Ser Gln Thr
            420                 425                 430

Gln Gln Gln Val Asp Arg Gln Ser Tyr Ile Asn Pro Ser Ser Ser Pro
        435                 440                 445

Gln Pro Leu Ser Ser Thr Ile Glu His Ala Lys Asp Arg Val Leu Thr
    450                 455                 460

Leu Asp Pro Gln Tyr Arg His Ala Gln Ala Ala Gln Asn Met Ser Gly
465                 470                 475                 480

Pro Asp Ala Glu Thr Asn Gln Lys Pro Val Asp Pro Ile Leu Gln Ala
                485                 490                 495

Phe Lys Asp Leu Lys Ala Leu Ile Asn Ser Val Ile Ala Gly Asp Asp
            500                 505                 510

Ser Phe Lys Ile Trp Gln Gln Gln Asn Pro Ser Lys Asn Leu Asp Asp
        515                 520                 525

Phe Lys His Asn Pro Thr Gln Met Asp Ser Leu Ser Gln Glu Thr Lys
    530                 535                 540

Glu Leu Leu Ser Ser Leu Gly Ser Glu Gly Tyr Ala Asn Ile Met Gly
545                 550                 555                 560

Ser Ala Ala Asn Ile Asp Pro Ala Gln Gln Met Ser Phe Ala Val Ser
                565                 570                 575

Phe Ser Thr Leu Asp Trp Gly Ser Gln Ala Asn Ser Val Gly Asn Thr
            580                 585                 590

Ile Gln Lys Thr Ile Thr Asn Asp Ala Gly Glu Lys Val Thr Asp Leu
        595                 600                 605

Ile Ser His Met His Lys Thr Gln Leu Ser Ala Asn Val Asn Gly Val
    610                 615                 620

Thr Lys Thr Val Thr Lys His Arg Thr Ile Asp Ile Pro Arg Ala Val
625                 630                 635                 640

Glu Glu Asn Lys Gly Pro Leu Asp Leu Ala Leu Val Ala Gln Asp Ala
                645                 650                 655

Thr Gly Lys Asn Met Ser Glu Ser Lys Ala Val Tyr Leu Thr Ala His
            660                 665                 670

Tyr Asn Gln Glu Gly Lys Leu Val Glu Ile Thr His Pro Glu Pro Met
```

-continued

```
        675                 680                 685

Leu Phe Phe Ser Asp Glu Pro Ser Ser Pro Ala Tyr Thr Val Ile Asn
    690                 695                 700

Asn Glu Val Tyr Thr Leu Pro Ile Thr Arg Glu Lys Tyr Asp Gln Leu
705                 710                 715                 720

Thr Lys Glu Ile Ser Gln Asn Ile Gln Glu Gln Asp Lys Asp Lys Glu
                725                 730                 735

Arg Glu Gln Glu Ala Val Asp Lys Phe Thr Val Gly Ser Arg Gln Thr
            740                 745                 750

Asp Ile His Asn Glu Lys Ser Ile Gln His Ala Asp Glu Val Ser Lys
        755                 760                 765

Asp Ala Pro Lys Ser Leu Lys Ser Ile Ala His Asp Glu Asn Lys Asn
    770                 775                 780

Lys Ile Gln Gly Thr Asp His Lys Ser Lys Asn Ser Asn Glu Tyr Val
785                 790                 795                 800

Gln His Met Ile Asn Ser Phe Asn Gln Asn Tyr Asn Lys Ile Asp Ser
                805                 810                 815

Asn Glu Pro Asn Arg Thr Glu Gln Val Lys Leu Lys Pro Val Val Lys
            820                 825                 830

Ser Ile Pro Glu Ser Pro Lys Asn Ser Thr Gln Ile Asp Pro Asn Glu
        835                 840                 845

Glu Gly Ser Ile Gly Tyr Val Lys Arg Val Ile Glu Ser Met Glu Gln
    850                 855                 860

Thr Ser Pro Asn Pro Ser Glu Ile Ala Gln Arg Leu Gln Val Asn Leu
865                 870                 875                 880

Ala Asn Ser Ser Gln Arg Ser Ser Ser Met Ser Ile Asn Thr Pro Thr
                885                 890                 895

Asn Thr Pro Arg Asn Asn Asn Gln Ser Lys Ser Gln Thr Lys Gly Ile
            900                 905                 910

Gly


<210> SEQ ID NO 9
<211> LENGTH: 949
<212> TYPE: PRT
<213> ORGANISM: Orientia tsutugamushi

<400> SEQUENCE: 9

Met Ala Pro Asp Asn Lys Pro Ile Asn Asn Lys Ser Ser Gly Leu Ile
1               5                   10                  15

Ser Lys Ser Gln Glu Gln Asn Ile Lys Asp Leu Gly Lys Lys Ile Asp
            20                  25                  30

Leu Met Ile Gln Gln Val Asp Thr Leu Asp Ser Lys Met Arg Ser Arg
        35                  40                  45

Ser Ala Glu Gly Asn Thr Leu Asp Val Lys Val Ile Arg Ala Leu Asn
    50                  55                  60

Asn Val Met Lys Ser Val Pro Glu Thr Leu Gln Gln Phe Ser Gln Glu
65                  70                  75                  80

Ile Leu Gln Gln Ser Lys Leu Ala Arg Gln Gln Pro Gln Asn Gly Gln
                85                  90                  95

Tyr Asn Asp Ala Phe Arg Lys Lys Arg Ala Glu Ala Lys Glu Lys Lys
            100                 105                 110

Glu Arg Leu Glu Lys Gln Lys Gln Glu Phe Met Gly Leu Val Ser Lys
        115                 120                 125

Leu Gly Glu Glu Met Lys Leu Val Gly Lys Pro Gly Gly Gln Ile Ser
```

-continued

```
    130                 135                 140

Glu Ile Lys Asp Thr Ile Asp Lys Leu His Ala Ile Val Asn Lys Ser
145                 150                 155                 160

Ala Gln His Gln Leu Gln Lys Thr Leu Gly Glu Leu Gln Ala Met Ile
                165                 170                 175

Asn Glu His Lys Gln Asn Gln Leu Gln Asp Ala Leu Asp Asp Leu Glu
            180                 185                 190

Asn Ile Ile Asn Asp His Lys Gln Asn Gln Lys Glu Gln Lys Ser Thr
        195                 200                 205

Ile Pro Pro Glu Lys His Thr His Asp Val Thr Ser Ile Lys Asn Gln
    210                 215                 220

Ala Gln Gln Asn Thr Gly Ile Thr Gln Pro Asp Ala Pro Lys Ser Ala
225                 230                 235                 240

Ser Lys Ser Ala Ala Asp Ile Ser Gln Ser Pro Gln Arg Ser Ser Pro
                245                 250                 255

Ala Thr Pro Thr Gly Thr Gly Gln Gln His Glu Gln Lys Lys Thr Pro
            260                 265                 270

Pro Pro Val Pro Pro Lys Pro Ser Lys Asn Thr Ile Glu Ala Ile Asn
        275                 280                 285

Ala Lys Ile Ala Gln Ala Gln Gln Asn Ala Gly Ile Asn Gln Pro Asp
    290                 295                 300

Ile Ala Lys Ser Ala Ser Lys Ser Ala Ala Asp Ile Pro Gln Ser Pro
305                 310                 315                 320

Gln His Ser Ser Pro Val Thr Pro Thr Ala Thr Val Gln Gln His Glu
                325                 330                 335

Pro Gln Lys Thr Thr Pro Pro Val Pro Pro Lys Pro Ser Lys Asn Ile
            340                 345                 350

Ile Glu Glu Leu Asn Ala Lys Ile Ala Gln Ala Gln Gln Asn Ala Gly
        355                 360                 365

Ile Asn Gln Pro Asp Ala Pro Lys Ser Ala Ser Lys Ser Ala Glu Asp
    370                 375                 380

Ile Ser Gln Ser Thr Gln His Ser Ser Pro Val Thr Pro Thr Ala Thr
385                 390                 395                 400

Ala Gln Gln His Glu Pro Gln Lys Thr Pro Pro Pro Val Pro Pro Lys
                405                 410                 415

Pro Ser Lys Asn Ile Ile Glu Glu Leu Lys Ala Lys Ile Ser Gln Thr
            420                 425                 430

Gln Gln Gln Val Asn Gln Gln Ser Tyr Ile Asn Pro Ser Ser Ser Pro
        435                 440                 445

Lys Pro Leu Ser Ser Thr Ile Glu His Ala Lys Asp Arg Val Leu Ile
    450                 455                 460

Ser Asp Pro Gln Tyr Arg His Ala Gln Ala Ala Gln Asn Met Ser Gly
465                 470                 475                 480

Pro Glu Ala Glu Thr Asn Gln Met Pro Val Asp Gln Ile Leu Gln Ala
                485                 490                 495

Phe Lys Asp Leu Lys Ala Leu Ile Asn Ser Val Ile Ala Glu Asp Asp
            500                 505                 510

Lys Phe Lys Val Trp Gln Gln Gln Asn Gln Ser Lys Ser Leu Asp Asp
        515                 520                 525

Phe Lys Arg Asp Thr Thr Gln Met Asp Ser Leu Ser Gln Glu Thr Lys
    530                 535                 540

Glu Leu Leu Ser Ser Ile Gly Ser Ala Gly Tyr Ala Asn Ile Met Gly
545                 550                 555                 560
```

-continued

```
Ser Thr Ala Asn Ile Glu Gln Ala Gln Gln Met Ser Phe Ala Ala Ser
                565                 570                 575

Phe Ser Thr Leu Asp Trp Ala Thr His Ala Asn Ser Val Gly Asn Thr
            580                 585                 590

Thr Gln Lys Thr Ile Thr Asn Asp Ala Gly Glu Lys Val Thr Asp Leu
        595                 600                 605

Ile Ser His Ser His Lys Thr Gln Leu Ser Ala Ser Val Asn Gly Val
    610                 615                 620

Thr Lys Thr Val Thr Lys His Arg Thr Ile Asp Ile Pro Arg Ala Val
625                 630                 635                 640

Glu Lys Asn Lys Gly Pro Leu Asp Leu Ala Leu Val Ala Gln Asp Glu
                645                 650                 655

Thr Gly Lys Asn Met Ser Glu Ser Lys Ala Val Tyr Leu Thr Ala His
            660                 665                 670

Tyr Asn Gln Glu Gly Lys Leu Val Glu Met Thr His Pro Glu Pro Leu
        675                 680                 685

Arg Phe Phe Ser Asp Glu Pro Gly Ser Pro Ala Tyr Thr Val Ile Asn
    690                 695                 700

Asn Glu Val Tyr Thr Leu Pro Ile Thr Lys Glu Lys Tyr Glu Gln Leu
705                 710                 715                 720

Thr Lys Glu Ile Ser Gln Asn Ile Gln Glu Gln Asp Lys Asp Lys Asp
                725                 730                 735

Ile Glu Gln Glu Ala Met Asp Lys Phe Thr Val Gly Ser Arg Gln Thr
            740                 745                 750

Asp Ile His Lys Glu Lys Ser Ile Gln Gln Ala Asp Glu Val Ser Thr
        755                 760                 765

Asp Glu Pro Lys Ser Leu Lys Ser Met Asn Glu Phe Thr Ile Ala Ser
    770                 775                 780

Arg Gln Thr Asp Asp Ile Tyr Asn Glu Lys Ser Thr Arg Asn Pro Glu
785                 790                 795                 800

Glu Ile Ser Ser Asp Ala Pro Lys Ser Leu Lys Ser Ile Ala Pro Asp
                805                 810                 815

Glu Asn Lys Asn Lys Ile Gln Ser Thr Asp His Lys Ser Lys Asn Ser
            820                 825                 830

Asn Glu Tyr Val Gln His Met Ile Asn Ser Phe Asn Gln Asn Tyr Asn
        835                 840                 845

Lys Ile Asp Ser Asn Glu Pro Asn Arg Thr Glu Gln Val Lys Leu Lys
    850                 855                 860

Pro Val Val Lys Ser Ile Pro Glu Ser Pro Lys Asn Ser Thr Gln Ile
865                 870                 875                 880

Asp Pro Asn Asp Glu Gly Ser Ile Gly Tyr Val Lys Arg Val Val Lys
                885                 890                 895

Ser Met Glu Gln Thr Ser Pro Ser Pro Ser Glu Ile Ala Gln Arg Leu
            900                 905                 910

Gln Leu Asn Leu Ala Asn Ser Ser Gln Arg Ser Ser Ser Met Ser Ile
        915                 920                 925

Asn Thr Pro Thr Asn Thr Pro Arg Asn Asn Asn Gln Ser Lys Ser Gln
    930                 935                 940

Thr Lys Gly Ile Gly
945
```

<210> SEQ ID NO 10
<211> LENGTH: 953

-continued

<212> TYPE: PRT
<213> ORGANISM: Orientia tsutugamushi

<400> SEQUENCE: 10

```
Met Ala Pro Asp Asn Lys Pro Ile Asn Thr Lys Ser Ser Gly Leu Ile
1               5                   10                  15

Ser Lys Ser Gln Glu Gln Asn Ile Lys Asp Leu Gly Lys Lys Ile Asp
            20                  25                  30

Leu Met Ile Gln Gln Ile Asp Thr Leu Asp Ser Lys Met Arg Ser Arg
        35                  40                  45

Ser Ala Glu Gly Ser Ala Leu Asn Val Lys Val Ile Arg Ala Leu Asn
    50                  55                  60

Asn Val Met Lys Asn Val Pro Glu Thr Leu Gln Gln Phe Ser Gln Glu
65                  70                  75                  80

Ile Leu Gln Gln Ser Lys Leu Ala Arg Gln Gln Pro Gln Lys Gly Gln
                85                  90                  95

Tyr Asn Asp Ala Phe Arg Lys Lys Arg Ala Glu Ala Lys Glu Lys Lys
            100                 105                 110

Gly His Leu Glu Lys Gln Lys Lys Glu Phe Met Gly Leu Val Ser Lys
        115                 120                 125

Leu Gly Glu Glu Met Lys Leu Val Gly Lys Ser Gly Gly Gln Met Ser
    130                 135                 140

Glu Ile Lys Asp Thr Leu Gly Lys Leu Gln Ala Ile Ile Asn Lys Gln
145                 150                 155                 160

Thr Gln Gln Gln Leu Gln Asn Thr Leu Thr Asp Leu Gln Lys Ile Ile
                165                 170                 175

Asn Glu His Lys Gln Ser Gln Leu Gln Glu Ala Leu Asp Asp Leu Glu
            180                 185                 190

Asn Ile Ile Asn Asp His Lys Gln Asn Gln Lys Glu Gln Lys Ala Pro
        195                 200                 205

Ile Pro Pro Glu Lys His Ala His Asp Val Thr Pro Ile Lys Asn Gln
    210                 215                 220

Ala Gln Gln Asn Ala Gly Ile Asn Gln Pro Asp Ala Pro Lys Ser Ala
225                 230                 235                 240

Ser Lys Ser Ala Ala Asp Ile Ser Gln Ser Thr Gln His Ser Ser Ser
                245                 250                 255

Ser Thr Pro Thr Ala Thr Ala Gln Gln Gln Glu Pro Gln Lys Thr Pro
            260                 265                 270

Pro Pro Val Pro Pro Lys Pro Asn Lys Asn Thr Ile Glu Glu Leu Lys
        275                 280                 285

Ala Arg Val Ala Gln Ala Gln Gln Asn Ala Gly Ile Ser Gln Pro Asp
    290                 295                 300

Ala Pro Lys Ser Ala Ser Lys Ser Ala Ala Gly Ile Ser Gln Ser Thr
305                 310                 315                 320

Gln His Ser Ser Ser Ser Thr Pro Thr Ala Thr Val Gln Gln Gln Glu
                325                 330                 335

Gln Lys Lys Thr Pro Pro Pro Val Pro Pro Lys Pro Ser Lys Asp Thr
            340                 345                 350

Ile Glu Thr Ile Lys Ala Lys Val Ala Gln Ala Gln Gln Asn Ala Gly
        355                 360                 365

Ile Ser Gln Pro Asp Thr Pro Lys Ser Ala Ser Lys Ser Ala Ala Asp
    370                 375                 380

Ile Ser Gln Ser Thr Gln Asn Ser Ser Pro Val Thr Pro Thr Ala Thr
385                 390                 395                 400
```

-continued

```
Val Gln Gln Gln Glu Gln Lys Lys Thr Pro Pro Pro Val Pro Pro Lys
                405                 410                 415

Pro Ser Lys Asn Ile Ile Glu Glu Leu Lys Ala Lys Ile Ser Gln Thr
            420                 425                 430

Gln Gln His Val Asn Gln Gln Ser Tyr Ile Asn Pro Ser Ser Ser Pro
        435                 440                 445

Gln Pro Leu Ser Ser Thr Ile Glu His Ala Lys Asp Arg Val Leu Thr
    450                 455                 460

Leu Asp Pro Gln His Arg Gln Ala Gln Ala Ala Gln Thr Ala Gln Ala
465                 470                 475                 480

Met Ser Gly Pro Asp Ala Glu Thr Asn Gln Met Pro Val Asp Pro Ile
                485                 490                 495

Leu Gln Ala Phe Lys Asp Leu Lys Ala Leu Ile Asn Ser Val Ile Ala
            500                 505                 510

Glu Asp Asn Lys Phe Lys Ala Trp Gln Gln Gln Asn Pro Ser Lys Ser
        515                 520                 525

Leu Asp Asp Phe Lys His Asp Ser Thr Gln Met Asp Ser Leu Ser Gln
    530                 535                 540

Glu Thr Lys Glu Leu Leu Ser Ser Leu Gly Tyr Glu Gly Tyr Ala Asn
545                 550                 555                 560

Ile Met Gly Ser Ala Ala Asn Ile Asp Ser Ala Gln Gln Met Ser Phe
                565                 570                 575

Ala Ala Ser Phe Ser Thr Leu Asp Trp Asp Thr Gln Ala Asn Ser Val
            580                 585                 590

Gly Asn Thr Ala Gln Lys Thr Ile Thr Asn Glu Ala Gly Glu Lys Val
        595                 600                 605

Thr Glu Leu Val Ser His Ser Asn Lys Val Gln Leu Ser Ala Ser Val
    610                 615                 620

Asn Gly Val Thr Lys Thr Val Thr Lys His Arg Thr Ile Asp Ile Pro
625                 630                 635                 640

Ser Ala Val Lys Glu Asn Lys Gly Pro Leu Asp Leu Ala Leu Val Ala
                645                 650                 655

Gln Asp Ala Thr Gly Lys Asn Met Pro Glu Ser Lys Ala Val Tyr Leu
            660                 665                 670

Thr Ala His Tyr Asn Gln Glu Gly Lys Leu Val Glu Met Thr His Pro
        675                 680                 685

Glu Pro Leu Arg Phe Phe Ser Asp Glu Pro Ser Ser Pro Ala Tyr Thr
    690                 695                 700

Val Ile Asn Asn Glu Val Tyr Thr Leu Pro Ile Thr Arg Glu Lys Tyr
705                 710                 715                 720

Asp Gln Leu Thr Lys Glu Ile Ser Gln Asn Ile Gln Glu Gln Asp Lys
                725                 730                 735

Asp Lys Glu Arg Glu Gln Glu Ala Val Asp Lys Phe Thr Val Gly Ser
            740                 745                 750

Arg Gln Thr Asp Ile His Lys Glu Lys Ser Ile Gln Gln Ala Asp Glu
        755                 760                 765

Val Ser Asn Asp Ala Pro Lys Ser Leu Lys Ser Met Asn Glu Phe Thr
    770                 775                 780

Ile Gly Ser Arg Gln Thr Cys Asp Ile Tyr Gln Glu Lys Ser Thr Gln
785                 790                 795                 800

Glu Ile Asp Lys Ile Ser Ser Asp Asp Pro Lys Ser Leu Lys Ser Ile
                805                 810                 815
```

-continued

```
Ala Pro Asp Glu Asn Gln Asn Lys Ile Gln Ser Arg Pro Asp Tyr Lys
            820                 825                 830

Leu Gln Asn Ser Asn Glu Tyr Val Gln His Met Ile Lys Ser Leu Asp
        835                 840                 845

Gln Asn Tyr His Lys Ile Asp Ser Asn Lys Gln Asn Cys Thr Glu Gln
    850                 855                 860

Val Lys Leu Lys Pro Val Val Lys Ser Met Pro Glu Ser Pro Lys Asn
865                 870                 875                 880

Ser Thr Gln Ile Asp Pro Asn Glu Glu Gly Ser Ile Gly Tyr Val Lys
                885                 890                 895

Arg Val Val Glu Ser Met Glu Gln Thr Ser Pro Asn Pro Ser Glu Ile
            900                 905                 910

Ala Gln Arg Leu Gln Leu Asn Leu Ala Asn Ser Ser Gln His Ser Ser
        915                 920                 925

Ser Thr Ser Ile Thr Thr Pro Thr Asn Thr Pro Arg Asn Asn Asn Gln
    930                 935                 940

Ser Lys Ser Gln Thr Lys Gly Ile Gly
945                 950
```

<210> SEQ ID NO 11
<211> LENGTH: 1350
<212> TYPE: DNA
<213> ORGANISM: Orientia tsutugamushi

<400> SEQUENCE: 11

```
atgggtggac agatgtctga gataaaagat actctagata agctttatgc aatagttaac      60

aagtcagcac agcatcaact gcaaaaaact cttggtgagc ttcaggcaat gattaatgaa     120

cataaacaga accagctaca agatgctcta gacgatctgg aaaatataat caacgatcat     180

aaacagaatc aaaaagaaca gaaggctcct atttcacctg aaacacatgc acataatgta     240

acgtctatta aaaaccaagc tcaacaaaat gctggtatta atcaaccgga tgcacctaaa     300

tctgctagca aatcagcagc agatatatca caatctactc agaattcttc tccagcgaca     360

ccaactggca cagggcaaca acaagagcca caaaaaaacgc ctcctcctgt tccacctaaa    420

cctagtaaaa atacaataga ggaattaaag gctaaaatag ctcaagctca acaaaatgct     480

ggtattaatc aaccaggtgc acctaaatct gctagcaaac cagcagcaga tataccacaa     540

tctactcagc attcttctcc agcaacatca actggcacag ggcaacaaca agagccacaa     600

aaaacacctc ctcctgttcc gcccaaacct agtaaagata caatagagga attaaaggct     660

aaaatagctc aagctcaaca aaatgctggt attaatcaac cagatgcgcc taaatctgct     720

agcaaatcag cagaagatat attacaatct actcagcatt cttctccagt aacaccaact     780

gctacagcac aacaacatga gccacaaaaa acacctcctc ctgttccacc taaacctagt     840

aaaaatataa tcgaagaatt aaaagctaag atatcacaaa ctcaacaaca ggttgaccgg     900

caatcatata ttaatccaag tagtagtccc caacctctta gttcaactat agagcatgct     960

aaagacagag tattaacatt agatccacaa tatagacacg ctcaagctgc tcaaaatatg    1020

agtggaccag atgctgaaac aaatcagaag ccagtagatc caattctaca ggcatttaaa    1080

gatttaaaag ctctaataaa tagcgtgatt gctggagatg atagtttcaa aatatggcaa    1140

cagcaaaatc caagcaaaaa tctagatgat tttaaacata atccaacgca aatggatagc    1200

ttatctcaag agactaaaga gttactatct agccttggat ctgaaggata tgctaatatt    1260

atgggttcag cagcaaatat tgatccagct cagcaaatgt catttgctgt atcttttagt    1320
```

-continued

```
acattagatt gggggagtca ggctaattaa                                    1350

<210> SEQ ID NO 12
<211> LENGTH: 1194
<212> TYPE: DNA
<213> ORGANISM: Orientia tsutugamushi

<400> SEQUENCE: 12

atggtgattg ctggagatga tagtttcaaa atatggcaac agcaaaatcc aagcaaaaat     60

ctagatgatt ttaaacataa tccaacgcaa atggatagct tatctcaaga gactaaagag    120

ttactatcta gccttggatc tgaaggatat gctaatatta tgggttcagc agcaaatatt    180

gatccagctc agcaaatgtc atttgctgta tcttttagta cattagattg ggggagtcag    240

gctaattctg ttggcaatac tattcaaaaa actattacca atgatgctgg tgaaaaagtt    300

acagacctta taagccatat gcataaaact cagctcagtg ctaatgttaa tggtgttaca    360

aaaactgtta ctaaacaccg taccatagat attccaaggg cagttgaaga aaacaaagga    420

cctttagatc ttgccttagt agcacaagat gcaacaggaa aaaatatgtc tgagtcaaaa    480

gcagtgtatc taactgctca ttataaccaa gaagggaaat tagtagaaat tactcatccg    540

gaaccgatgc tattttttag tgatgagcct agctctccag cttatacagt tataaataat    600

gaagtttata ctttgccaat tactagagaa aaatatgacc agctaaccaa agaaatatca    660

caaaatatac aggaacaaga caaagataaa gagagagaac aggaagctgt ggataagttt    720

acagtgggtt ctcgtcaaac tgatattcat aacgaaaaaa gtattcaaca tgctgatgaa    780

gtaagtaagg atgctcctaa atctttaaaa tctattgctc atgatgaaaa caaaaaataaa   840

attcaaggca ctgatcataa atcgaaaaac agcaatgaat atgttcaaca tatgattaac    900

tcgtttaatc aaaactataa caaaattgat tctaacgagc caaatcgtac tgaacaggta    960

aaactgaagc ctgtagtcaa atcaatacca gaatctccaa aaaactctac tcagattgat   1020

cctaatgaag aaggtagtat tggatacgta aaacgtgtaa ttgaatcaat ggaacaaaca   1080

tcaccaaatc ctagtgaaat agcacaaaga ttacaggtaa atctagctaa tagttctcag   1140

cgtagttcta gtatgtctat taatactcct actaatactc ctcgcaataa ttag         1194

<210> SEQ ID NO 13
<211> LENGTH: 1350
<212> TYPE: DNA
<213> ORGANISM: Orientia tsutugamushi

<400> SEQUENCE: 13

atgggtggac agatatctga gataaaagat actattgata agcttcatgc aatagttaac     60

aagtcagcac agcatcaact gcaaaaaact cttggtgagc ttcaggcaat gattaatgaa    120

cataaacaga accagctaca agatgctcta gatgatctgg aaaatataat caacgatcat    180

aaacagaatc aaaaagaaca gaagtctact attccacctg aaaaacatac acatgatgta    240

acatctatta aaaaccaagc tcaacaaaat actggtatta ctcaaccaga tgcacctaaa    300

tctgctagca aatcagcagc agatatatca caatctcctc agcgttcttc tccagcaacg    360

ccaactggca cagggcaaca acatgaacaa aaaaaaacac ctcctcctgt tccacctaaa    420

cctagtaaaa atacaatcga agctataaat gctaaaatag ctcaagctca acaaaatgct    480

ggtattaatc aaccagatat agctaaatct gctagcaaat cagcagcaga tataccacaa    540

tctcctcagc attcttctcc agtaacacca actgctacag tgcaacaaca cgagccacaa    600

aaaacgactc ctcctgttcc acctaaacct agtaaaaata taatcgaaga attaaatgct    660
```

```
aaaatagctc aagctcaaca aaatgctggt attaatcaac cagatgcacc taaatctgct    720

agcaaatcag cagaagatat atcacaatct actcagcatt cttctccagt aacaccaact    780

gctacagcac aacaacatga gccacaaaaa acacctcctc ctgttccacc taaacctagt    840

aaaaatataa tcgaagaatt aaaagctaag atatcacaaa ctcaacaaca ggttaatcag    900

caatcatata ttaatccaag tagtagtccc aaacctctta gttcaactat agagcatgct    960

aaagacagag tattaatatc agatccacaa tatagacatg ctcaagctgc tcaaaatatg   1020

agtggaccag aggctgaaac aaatcagatg ccagtagatc aaattctaca agcatttaaa   1080

gatttaaaag cacttataaa tagtgtgatt gctgaagatg ataagtttaa agtatggcaa   1140

cagcaaaatc aaagcaaaag cctagatgat tttaaacgtg atacaacaca aatggatagc   1200

ttatctcaag agactaaaga gttactatct agcatcggat ctgcaggata tgctaacatt   1260

atgggctcaa cagcaaatat tgaacaagct cagcaaatgt catttgctgc atcttttagt   1320

acattagatt gggctactca tgctaattaa                                    1350
```

<210> SEQ ID NO 14
<211> LENGTH: 1301
<212> TYPE: DNA
<213> ORGANISM: Orientia tsutugamushi

<400> SEQUENCE: 14

```
atggtgattg ctgaagatga taagtttaaa gtatggcaac agcaaaatca aagcaaaagc     60

ctagatgatt ttaaacgtga tacaacacaa atggatagct tatctcaaga gactaaagag    120

ttactatcta gcatcggatc tgcaggatat gctaacatta tgggctcaac agcaaatatt    180

gaacaagctc agcaaatgtc atttgctgca tcttttagta cattagattg ggctactcat    240

gctaattctg ttggcaatac tactcaaaaa actattacca atgatgctgg tgaaaaagtt    300

acagacctta taagccatag ccataaaact cagctcagtg ctagtgttaa tggtgttaca    360

aaaactgtta ctaaacaccg taccatagat attccaaggg cagttgaaaa aaacaaagga    420

cctttagatc ttgctttagt agcacaagat gaaactggaa aaaatatgtc tgagtcaaaa    480

gcagtgtatc taactgctca ttataaccaa gaaggaaaat tagtagaaat gactcatcct    540

gaacctctga gattctttag tgatgagcct ggctctccag cttatacagt tataaataat    600

gaagtttata ctttgccaat tactaaagaa aaatatgaac agctaaccaa agaaatatca    660

caaaatatac aggaacagga taaagataaa gacatagaac aggaagctat ggataagttt    720

acagtaggtt ctcgtcaaac tgatattcat aaagaaaaaa gtattcaaca ggctgatgaa    780

gtaagtactg atgagcctaa atccttaaag tctatgaatg agtttacaat agcctctcgt    840

caaactgatg atatctataa cgagaaaagt actcgaaatc ctgaagaaat aagtagcgat    900

gctcctaaat ctttaaaatc tattgctcct gatgaaaaca aaaataaaat tcaaagcact    960

gatcataaat cgaaaaacag caatgaatat gttcaacata tgattaactc gtttaatcaa   1020

aactataaca aaattgattc taacgaacca aatcgtactg aacaggtaaa actgaagcct   1080

gtagtcaaat caataccaga atctccaaaa aactctactc agattgatcc taatgatgaa   1140

ggtagtattg gatatgtaaa acgtgtagtt aaatcaatgg aacaaacatc accaagtcct   1200

agtgagatag cacaaagatt gcagttaaat ctagctaata gttctcagcg tagttctagt   1260

atgtctatta atactcctac taatactcct cgcaataata g                       1301
```

<210> SEQ ID NO 15

-continued

<211> LENGTH: 1149
<212> TYPE: DNA
<213> ORGANISM: Orientia tsutugamushi

<400> SEQUENCE: 15

```
atgggtggac agatgtctga gataaaagat actctaggta agcttcaagc aataattaat     60

aagcagaccc aacagcaact acaaaatact ctgactgatc tacagaaaat aattaatgaa    120

cacaaacaga gccagctaca agaggctcta gatgatctgg aaaatataat caacgatcat    180

aaacagaatc aaaaagaaca gaaggcccct attccacctg aaaaacatgc acatgatgta    240

acacctatta aaaatcaagc tcaacaaaat gctggtatta accaaccaga tgcacctaag    300

tctgctagca aatcagcagc agatatatca caatctactc agcattcttc ttcgtctaca    360

ccaactgcta cagcgcaaca acaagagcca caaaaaacgc ctcctcctgt tccacctaaa    420

cctaataaaa atacaataga ggaattaaag gctagagtag ctcaagccca acaaaatgct    480

ggtattagtc aaccagatgc gcctaaatct gctagcaaat cagcagcagg tatatcacaa    540

tctactcagc attcttcttc gtctacacca actgctacag tgcaacaaca agagcaaaaa    600

aaaacgcctc ctcctgttcc gcctaaacct agtaaagata caatcgaaac tataaaagct    660

aaagtagctc aagctcaaca aaatgctggt attagtcaac cagatacacc taaatctgct    720

agcaaatcag cagcagatat atcacagtct actcagaatt cttctccagt aacaccaact    780

gctacagtgc aacaacaaga gcaaaaaaaa acgcctcctc ctgttccacc taaacctagt    840

aaaaatataa tcgaagaatt aaaagctaag atatcacaaa ctcaacaaca tgttaatcag    900

caatcatata ttaatccaag tagtagtcca caacctctta gttcgactat agagcatgct    960

aaagacagag tattaacatt agatccacaa catagacaag cgcaagctgc ccaaactgcc   1020

caagctatga gtggaccaga tgctgaaaca aatcagatgc cagtagatcc aattctacaa   1080

gcatttaaag atttaaaagc gcttataaat agtgtaattg ctgaagataa taagtttaag   1140

gcatggtaa                                                           1149
```

<210> SEQ ID NO 16
<211> LENGTH: 1328
<212> TYPE: DNA
<213> ORGANISM: Orientia tsutugamushi

<400> SEQUENCE: 16

```
atggatttaa aagcgcttat aaatagtgta attgctgaag ataataagtt taaggcatgg     60

caacagcaaa atccaagcaa aagtctagat gattttaaac atgattcaac gcaaatggat    120

agcttatctc aagagactaa agagttacta tctagccttg gatacgaagg atatgctaac    180

attatgggtt cagcagcaaa tattgattca gctcagcaaa tgtcatttgc tgcatctttt    240

agtacattag attgggatac tcaagctaat tctgttggca atactgctca aaaaactatt    300

accaatgagg ctggtgaaaa agttacagaa ctcgtaagcc acagtaataa agttcagctt    360

agtgctagtg ttaatggcgt tacaaaaact gtcactaaac accgtactat agatattcca    420

agtgcagtta aagaaaacaa aggaccttta gatcttgcct tagtagcaca agatgcaact    480

ggaaaaaata tgcctgagtc aaaagcagta tatctaactg ctcattataa ccaagaagga    540

aaattagtag aaatgactca tccggaacct ctgagattct ttagtgatga gcctagctct    600

ccagcttata cagttataaa taatgaagtt tatactttgc caattactag agaaaaatat    660

gaccagctaa ccaaagaaat atcacaaaat atacaggaac aagataaaga taaagagaga    720

gaacaggaag ctgtggataa gtttacagta gggtctcgtc aaactgatat tcataaagaa    780
```

-continued

```
aaaagtattc aacaggctga tgaagtaagt aacgatgctc ctaaatcctt aaagtctatg    840

aatgagttta caataggctc tcgtcaaact tgcgatatct atcaagaaaa aagcactcaa    900

gaaattgata aaataagtag cgatgatcct aaatctttaa agtctattgc tcctgatgaa    960

aaccaaaaca aaattcaaag ccgacctgat tataaattgc aaaacagcaa tgaatatgtt   1020

caacatatga ttaaatcact tgatcaaaac tatcacaaaa ttgattctaa caaacaaaat   1080

tgtactgaac aggtaaaact gaagcctgta gtcaaatcaa tgccagaatc tccaaaaaac   1140

tctactcaga ttgatcctaa tgaggaaggt agtattggat atgtaaaacg tgtagttgaa   1200

tcaatggaac aaacatcacc aaatcctagt gagatagcac aaagattgca gttaaatcta   1260

gctaatagtt ctcagcatag ttctagtaca tctattacta ctcctactaa tactcctcgc   1320

aataatag                                                            1328
```

```
<210> SEQ ID NO 17
<211> LENGTH: 449
<212> TYPE: PRT
<213> ORGANISM: Orientia tsutugamushi

<400> SEQUENCE: 17

Met Gly Gly Gln Met Ser Glu Ile Lys Asp Thr Leu Asp Lys Leu Tyr
1               5                   10                  15

Ala Ile Val Asn Lys Ser Ala Gln His Gln Leu Gln Lys Thr Leu Gly
            20                  25                  30

Glu Leu Gln Ala Met Ile Asn Glu His Lys Gln Asn Gln Leu Gln Asp
        35                  40                  45

Ala Leu Asp Asp Leu Glu Asn Ile Ile Asn Asp His Lys Gln Asn Gln
    50                  55                  60

Lys Glu Gln Lys Ala Pro Ile Ser Pro Glu Thr His Ala His Asn Val
65                  70                  75                  80

Thr Ser Ile Lys Asn Gln Ala Gln Gln Asn Ala Gly Ile Asn Gln Pro
                85                  90                  95

Asp Ala Pro Lys Ser Ala Ser Lys Ser Ala Ala Asp Ile Ser Gln Ser
            100                 105                 110

Thr Gln Asn Ser Ser Pro Ala Thr Pro Thr Gly Thr Gly Gln Gln Gln
        115                 120                 125

Glu Pro Gln Lys Thr Pro Pro Pro Val Pro Pro Lys Pro Ser Lys Asn
    130                 135                 140

Thr Ile Glu Glu Leu Lys Ala Lys Ile Ala Gln Ala Gln Gln Asn Ala
145                 150                 155                 160

Gly Ile Asn Gln Pro Gly Ala Pro Lys Ser Ala Ser Lys Pro Ala Ala
                165                 170                 175

Asp Ile Pro Gln Ser Thr Gln His Ser Ser Pro Ala Thr Ser Thr Gly
            180                 185                 190

Thr Gly Gln Gln Gln Glu Pro Gln Lys Thr Pro Pro Pro Val Pro Pro
        195                 200                 205

Lys Pro Ser Lys Asp Thr Ile Glu Glu Leu Lys Ala Lys Ile Ala Gln
    210                 215                 220

Ala Gln Gln Asn Ala Gly Ile Asn Gln Pro Asp Ala Pro Lys Ser Ala
225                 230                 235                 240

Ser Lys Ser Ala Glu Asp Ile Leu Gln Ser Thr Gln His Ser Ser Pro
                245                 250                 255

Val Thr Pro Thr Ala Thr Ala Gln Gln His Glu Pro Gln Lys Thr Pro
            260                 265                 270
```

-continued

```
Pro Pro Val Pro Pro Lys Pro Ser Lys Asn Ile Ile Glu Glu Leu Lys
        275                 280                 285

Ala Lys Ile Ser Gln Thr Gln Gln Gln Val Asp Arg Gln Ser Tyr Ile
    290                 295                 300

Asn Pro Ser Ser Ser Pro Gln Pro Leu Ser Ser Thr Ile Glu His Ala
305                 310                 315                 320

Lys Asp Arg Val Leu Thr Leu Asp Pro Gln Tyr Arg His Ala Gln Ala
                325                 330                 335

Ala Gln Asn Met Ser Gly Pro Asp Ala Glu Thr Asn Gln Lys Pro Val
            340                 345                 350

Asp Pro Ile Leu Gln Ala Phe Lys Asp Leu Lys Ala Leu Ile Asn Ser
        355                 360                 365

Val Ile Ala Gly Asp Asp Ser Phe Lys Ile Trp Gln Gln Gln Asn Pro
    370                 375                 380

Ser Lys Asn Leu Asp Asp Phe Lys His Asn Pro Thr Gln Met Asp Ser
385                 390                 395                 400

Leu Ser Gln Glu Thr Lys Glu Leu Leu Ser Ser Leu Gly Ser Glu Gly
                405                 410                 415

Tyr Ala Asn Ile Met Gly Ser Ala Ala Asn Ile Asp Pro Ala Gln Gln
            420                 425                 430

Met Ser Phe Ala Val Ser Phe Ser Thr Leu Asp Trp Gly Ser Gln Ala
        435                 440                 445

Asn


<210> SEQ ID NO 18
<211> LENGTH: 397
<212> TYPE: PRT
<213> ORGANISM: Orientia tsutugamushi

<400> SEQUENCE: 18

Met Val Ile Ala Gly Asp Asp Ser Phe Lys Ile Trp Gln Gln Gln Asn
1               5                   10                  15

Pro Ser Lys Asn Leu Asp Asp Phe Lys His Asn Pro Thr Gln Met Asp
            20                  25                  30

Ser Leu Ser Gln Glu Thr Lys Glu Leu Leu Ser Ser Leu Gly Ser Glu
        35                  40                  45

Gly Tyr Ala Asn Ile Met Gly Ser Ala Ala Asn Ile Asp Pro Ala Gln
    50                  55                  60

Gln Met Ser Phe Ala Val Ser Phe Ser Thr Leu Asp Trp Gly Ser Gln
65                  70                  75                  80

Ala Asn Ser Val Gly Asn Thr Ile Gln Lys Thr Ile Thr Asn Asp Ala
                85                  90                  95

Gly Glu Lys Val Thr Asp Leu Ile Ser His Met His Lys Thr Gln Leu
            100                 105                 110

Ser Ala Asn Val Asn Gly Val Thr Lys Thr Val Thr Lys His Arg Thr
        115                 120                 125

Ile Asp Ile Pro Arg Ala Val Glu Glu Asn Lys Gly Pro Leu Asp Leu
    130                 135                 140

Ala Leu Val Ala Gln Asp Ala Thr Gly Lys Asn Met Ser Glu Ser Lys
145                 150                 155                 160

Ala Val Tyr Leu Thr Ala His Tyr Asn Gln Glu Gly Lys Leu Val Glu
                165                 170                 175

Ile Thr His Pro Glu Pro Met Leu Phe Phe Ser Asp Glu Pro Ser Ser
            180                 185                 190
```

-continued

```
Pro Ala Tyr Thr Val Ile Asn Asn Glu Val Tyr Thr Leu Pro Ile Thr
        195                 200                 205

Arg Glu Lys Tyr Asp Gln Leu Thr Lys Glu Ile Ser Gln Asn Ile Gln
    210                 215                 220

Glu Gln Asp Lys Asp Lys Glu Arg Glu Gln Glu Ala Val Asp Lys Phe
225                 230                 235                 240

Thr Val Gly Ser Arg Gln Thr Asp Ile His Asn Glu Lys Ser Ile Gln
                245                 250                 255

His Ala Asp Glu Val Ser Lys Asp Ala Pro Lys Ser Leu Lys Ser Ile
            260                 265                 270

Ala His Asp Glu Asn Lys Asn Lys Ile Gln Gly Thr Asp His Lys Ser
        275                 280                 285

Lys Asn Ser Asn Glu Tyr Val Gln His Met Ile Asn Ser Phe Asn Gln
    290                 295                 300

Asn Tyr Asn Lys Ile Asp Ser Asn Glu Pro Asn Arg Thr Glu Gln Val
305                 310                 315                 320

Lys Leu Lys Pro Val Val Lys Ser Ile Pro Glu Ser Pro Lys Asn Ser
                325                 330                 335

Thr Gln Ile Asp Pro Asn Glu Glu Gly Ser Ile Gly Tyr Val Lys Arg
            340                 345                 350

Val Ile Glu Ser Met Glu Gln Thr Ser Pro Asn Pro Ser Glu Ile Ala
        355                 360                 365

Gln Arg Leu Gln Val Asn Leu Ala Asn Ser Ser Gln Arg Ser Ser Ser
    370                 375                 380

Met Ser Ile Asn Thr Pro Thr Asn Thr Pro Arg Asn Asn
385                 390                 395


<210> SEQ ID NO 19
<211> LENGTH: 449
<212> TYPE: PRT
<213> ORGANISM: Orientia tsutugamushi

<400> SEQUENCE: 19

Met Gly Gly Gln Ile Ser Glu Ile Lys Asp Thr Ile Asp Lys Leu His
1               5                   10                  15

Ala Ile Val Asn Lys Ser Ala Gln His Gln Leu Gln Lys Thr Leu Gly
            20                  25                  30

Glu Leu Gln Ala Met Ile Asn Glu His Lys Gln Asn Gln Leu Gln Asp
        35                  40                  45

Ala Leu Asp Asp Leu Glu Asn Ile Ile Asn Asp His Lys Gln Asn Gln
    50                  55                  60

Lys Glu Gln Lys Ser Thr Ile Pro Pro Glu Lys His Thr His Asp Val
65                  70                  75                  80

Thr Ser Ile Lys Asn Gln Ala Gln Gln Asn Thr Gly Ile Thr Gln Pro
                85                  90                  95

Asp Ala Pro Lys Ser Ala Ser Lys Ser Ala Ala Asp Ile Ser Gln Ser
            100                 105                 110

Pro Gln Arg Ser Ser Pro Ala Thr Pro Thr Gly Thr Gly Gln Gln His
        115                 120                 125

Glu Gln Lys Lys Thr Pro Pro Pro Val Pro Pro Lys Pro Ser Lys Asn
    130                 135                 140

Thr Ile Glu Ala Ile Asn Ala Lys Ile Ala Gln Ala Gln Gln Asn Ala
145                 150                 155                 160

Gly Ile Asn Gln Pro Asp Ile Ala Lys Ser Ala Ser Lys Ser Ala Ala
```

-continued

```
                165                 170                 175

Asp Ile Pro Gln Ser Pro Gln His Ser Ser Pro Val Thr Pro Thr Ala
            180                 185                 190

Thr Val Gln Gln His Glu Pro Gln Lys Thr Thr Pro Pro Val Pro Pro
        195                 200                 205

Lys Pro Ser Lys Asn Ile Ile Glu Glu Leu Asn Ala Lys Ile Ala Gln
    210                 215                 220

Ala Gln Gln Asn Ala Gly Ile Asn Gln Pro Asp Ala Pro Lys Ser Ala
225                 230                 235                 240

Ser Lys Ser Ala Glu Asp Ile Ser Gln Ser Thr Gln His Ser Ser Pro
                245                 250                 255

Val Thr Pro Thr Ala Thr Ala Gln Gln His Glu Pro Gln Lys Thr Pro
            260                 265                 270

Pro Pro Val Pro Pro Lys Pro Ser Lys Asn Ile Ile Glu Glu Leu Lys
        275                 280                 285

Ala Lys Ile Ser Gln Thr Gln Gln Gln Val Asn Gln Gln Ser Tyr Ile
    290                 295                 300

Asn Pro Ser Ser Ser Pro Lys Pro Leu Ser Ser Thr Ile Glu His Ala
305                 310                 315                 320

Lys Asp Arg Val Leu Ile Ser Asp Pro Gln Tyr Arg His Ala Gln Ala
                325                 330                 335

Ala Gln Asn Met Ser Gly Pro Glu Ala Glu Thr Asn Gln Met Pro Val
            340                 345                 350

Asp Gln Ile Leu Gln Ala Phe Lys Asp Leu Lys Ala Leu Ile Asn Ser
        355                 360                 365

Val Ile Ala Glu Asp Asp Lys Phe Lys Val Trp Gln Gln Gln Asn Gln
    370                 375                 380

Ser Lys Ser Leu Asp Asp Phe Lys Arg Asp Thr Thr Gln Met Asp Ser
385                 390                 395                 400

Leu Ser Gln Glu Thr Lys Glu Leu Leu Ser Ser Ile Gly Ser Ala Gly
                405                 410                 415

Tyr Ala Asn Ile Met Gly Ser Thr Ala Asn Ile Glu Gln Ala Gln Gln
            420                 425                 430

Met Ser Phe Ala Ala Ser Phe Ser Thr Leu Asp Trp Ala Thr His Ala
        435                 440                 445

Asn


<210> SEQ ID NO 20
<211> LENGTH: 433
<212> TYPE: PRT
<213> ORGANISM: Orientia tsutugamushi

<400> SEQUENCE: 20

Met Val Ile Ala Glu Asp Asp Lys Phe Lys Val Trp Gln Gln Gln Asn
1               5                   10                  15

Gln Ser Lys Ser Leu Asp Asp Phe Lys Arg Asp Thr Thr Gln Met Asp
            20                  25                  30

Ser Leu Ser Gln Glu Thr Lys Glu Leu Leu Ser Ser Ile Gly Ser Ala
        35                  40                  45

Gly Tyr Ala Asn Ile Met Gly Ser Thr Ala Asn Ile Glu Gln Ala Gln
    50                  55                  60

Gln Met Ser Phe Ala Ala Ser Phe Ser Thr Leu Asp Trp Ala Thr His
65                  70                  75                  80

Ala Asn Ser Val Gly Asn Thr Thr Gln Lys Thr Ile Thr Asn Asp Ala
```

-continued

```
                85                  90                  95

Gly Glu Lys Val Thr Asp Leu Ile Ser His Ser His Lys Thr Gln Leu
            100                 105                 110

Ser Ala Ser Val Asn Gly Val Thr Lys Thr Val Thr Lys His Arg Thr
        115                 120                 125

Ile Asp Ile Pro Arg Ala Val Glu Lys Asn Lys Gly Pro Leu Asp Leu
    130                 135                 140

Ala Leu Val Ala Gln Asp Glu Thr Gly Lys Asn Met Ser Glu Ser Lys
145                 150                 155                 160

Ala Val Tyr Leu Thr Ala His Tyr Asn Gln Glu Gly Lys Leu Val Glu
                165                 170                 175

Met Thr His Pro Glu Pro Leu Arg Phe Phe Ser Asp Glu Pro Gly Ser
            180                 185                 190

Pro Ala Tyr Thr Val Ile Asn Asn Glu Val Tyr Thr Leu Pro Ile Thr
        195                 200                 205

Lys Glu Lys Tyr Glu Gln Leu Thr Lys Glu Ile Ser Gln Asn Ile Gln
    210                 215                 220

Glu Gln Asp Lys Asp Lys Asp Ile Glu Gln Glu Ala Met Asp Lys Phe
225                 230                 235                 240

Thr Val Gly Ser Arg Gln Thr Asp Ile His Lys Glu Lys Ser Ile Gln
                245                 250                 255

Gln Ala Asp Glu Val Ser Thr Asp Glu Pro Lys Ser Leu Lys Ser Met
            260                 265                 270

Asn Glu Phe Thr Ile Ala Ser Arg Gln Thr Asp Asp Ile Tyr Asn Glu
        275                 280                 285

Lys Ser Thr Arg Asn Pro Glu Glu Ile Ser Ser Asp Ala Pro Lys Ser
    290                 295                 300

Leu Lys Ser Ile Ala Pro Asp Glu Asn Lys Asn Lys Ile Gln Ser Thr
305                 310                 315                 320

Asp His Lys Ser Lys Asn Ser Asn Glu Tyr Val Gln His Met Ile Asn
                325                 330                 335

Ser Phe Asn Gln Asn Tyr Asn Lys Ile Asp Ser Asn Glu Pro Asn Arg
            340                 345                 350

Thr Glu Gln Val Lys Leu Lys Pro Val Val Lys Ser Ile Pro Glu Ser
        355                 360                 365

Pro Lys Asn Ser Thr Gln Ile Asp Pro Asn Asp Glu Gly Ser Ile Gly
    370                 375                 380

Tyr Val Lys Arg Val Val Lys Ser Met Glu Gln Thr Ser Pro Ser Pro
385                 390                 395                 400

Ser Glu Ile Ala Gln Arg Leu Gln Leu Asn Leu Ala Asn Ser Ser Gln
                405                 410                 415

Arg Ser Ser Ser Met Ser Ile Asn Thr Pro Thr Asn Thr Pro Arg Asn
            420                 425                 430

Asn

<210> SEQ ID NO 21
<211> LENGTH: 382
<212> TYPE: PRT
<213> ORGANISM: Orientia tsutugamushi

<400> SEQUENCE: 21

Met Gly Gly Gln Met Ser Glu Ile Lys Asp Thr Leu Gly Lys Leu Gln
1               5                   10                  15

Ala Ile Ile Asn Lys Gln Thr Gln Gln Gln Leu Gln Asn Thr Leu Thr
```

-continued

```
            20                  25                  30

Asp Leu Gln Lys Ile Ile Asn Glu His Lys Gln Ser Gln Leu Gln Glu
        35                  40                  45

Ala Leu Asp Asp Leu Glu Asn Ile Ile Asn Asp His Lys Gln Asn Gln
    50                  55                  60

Lys Glu Gln Lys Ala Pro Ile Pro Pro Glu Lys His Ala His Asp Val
65                  70                  75                  80

Thr Pro Ile Lys Asn Gln Ala Gln Gln Asn Ala Gly Ile Asn Gln Pro
                85                  90                  95

Asp Ala Pro Lys Ser Ala Ser Lys Ser Ala Ala Asp Ile Ser Gln Ser
            100                 105                 110

Thr Gln His Ser Ser Ser Ser Thr Pro Thr Ala Thr Ala Gln Gln Gln
        115                 120                 125

Glu Pro Gln Lys Thr Pro Pro Pro Val Pro Pro Lys Pro Asn Lys Asn
    130                 135                 140

Thr Ile Glu Glu Leu Lys Ala Arg Val Ala Gln Ala Gln Gln Asn Ala
145                 150                 155                 160

Gly Ile Ser Gln Pro Asp Ala Pro Lys Ser Ala Ser Lys Ser Ala Ala
                165                 170                 175

Gly Ile Ser Gln Ser Thr Gln His Ser Ser Ser Ser Thr Pro Thr Ala
            180                 185                 190

Thr Val Gln Gln Gln Glu Gln Lys Lys Thr Pro Pro Pro Val Pro Pro
        195                 200                 205

Lys Pro Ser Lys Asp Thr Ile Glu Thr Ile Lys Ala Lys Val Ala Gln
    210                 215                 220

Ala Gln Gln Asn Ala Gly Ile Ser Gln Pro Asp Thr Pro Lys Ser Ala
225                 230                 235                 240

Ser Lys Ser Ala Ala Asp Ile Ser Gln Ser Thr Gln Asn Ser Ser Pro
                245                 250                 255

Val Thr Pro Thr Ala Thr Val Gln Gln Gln Glu Gln Lys Lys Thr Pro
            260                 265                 270

Pro Pro Val Pro Pro Lys Pro Ser Lys Asn Ile Ile Glu Glu Leu Lys
        275                 280                 285

Ala Lys Ile Ser Gln Thr Gln Gln His Val Asn Gln Gln Ser Tyr Ile
    290                 295                 300

Asn Pro Ser Ser Ser Pro Gln Pro Leu Ser Ser Thr Ile Glu His Ala
305                 310                 315                 320

Lys Asp Arg Val Leu Thr Leu Asp Pro Gln His Arg Gln Ala Gln Ala
                325                 330                 335

Ala Gln Thr Ala Gln Ala Met Ser Gly Pro Asp Ala Glu Thr Asn Gln
            340                 345                 350

Met Pro Val Asp Pro Ile Leu Gln Ala Phe Lys Asp Leu Lys Ala Leu
        355                 360                 365

Ile Asn Ser Val Ile Ala Glu Asp Asn Lys Phe Lys Ala Trp
    370                 375                 380


<210> SEQ ID NO 22
<211> LENGTH: 442
<212> TYPE: PRT
<213> ORGANISM: Orientia tsutugamushi

<400> SEQUENCE: 22

Met Asp Leu Lys Ala Leu Ile Asn Ser Val Ile Ala Glu Asp Asn Lys
1               5                   10                  15
```

-continued

```
Phe Lys Ala Trp Gln Gln Gln Asn Pro Ser Lys Ser Leu Asp Asp Phe
            20                  25                  30

Lys His Asp Ser Thr Gln Met Asp Ser Leu Ser Gln Glu Thr Lys Glu
        35                  40                  45

Leu Leu Ser Ser Leu Gly Tyr Glu Gly Tyr Ala Asn Ile Met Gly Ser
    50                  55                  60

Ala Ala Asn Ile Asp Ser Ala Gln Gln Met Ser Phe Ala Ala Ser Phe
65                  70                  75                  80

Ser Thr Leu Asp Trp Asp Thr Gln Ala Asn Ser Val Gly Asn Thr Ala
                85                  90                  95

Gln Lys Thr Ile Thr Asn Glu Ala Gly Glu Lys Val Thr Glu Leu Val
            100                 105                 110

Ser His Ser Asn Lys Val Gln Leu Ser Ala Ser Val Asn Gly Val Thr
        115                 120                 125

Lys Thr Val Thr Lys His Arg Thr Ile Asp Ile Pro Ser Ala Val Lys
    130                 135                 140

Glu Asn Lys Gly Pro Leu Asp Leu Ala Leu Val Ala Gln Asp Ala Thr
145                 150                 155                 160

Gly Lys Asn Met Pro Glu Ser Lys Ala Val Tyr Leu Thr Ala His Tyr
                165                 170                 175

Asn Gln Glu Gly Lys Leu Val Glu Met Thr His Pro Glu Pro Leu Arg
            180                 185                 190

Phe Phe Ser Asp Glu Pro Ser Ser Pro Ala Tyr Thr Val Ile Asn Asn
        195                 200                 205

Glu Val Tyr Thr Leu Pro Ile Thr Arg Glu Lys Tyr Asp Gln Leu Thr
    210                 215                 220

Lys Glu Ile Ser Gln Asn Ile Gln Glu Gln Asp Lys Asp Lys Glu Arg
225                 230                 235                 240

Glu Gln Glu Ala Val Asp Lys Phe Thr Val Gly Ser Arg Gln Thr Asp
                245                 250                 255

Ile His Lys Glu Lys Ser Ile Gln Gln Ala Asp Glu Val Ser Asn Asp
            260                 265                 270

Ala Pro Lys Ser Leu Lys Ser Met Asn Glu Phe Thr Ile Gly Ser Arg
        275                 280                 285

Gln Thr Cys Asp Ile Tyr Gln Glu Lys Ser Thr Gln Glu Ile Asp Lys
    290                 295                 300

Ile Ser Ser Asp Asp Pro Lys Ser Leu Lys Ser Ile Ala Pro Asp Glu
305                 310                 315                 320

Asn Gln Asn Lys Ile Gln Ser Arg Pro Asp Tyr Lys Leu Gln Asn Ser
                325                 330                 335

Asn Glu Tyr Val Gln His Met Ile Lys Ser Leu Asp Gln Asn Tyr His
            340                 345                 350

Lys Ile Asp Ser Asn Lys Gln Asn Cys Thr Glu Gln Val Lys Leu Lys
        355                 360                 365

Pro Val Val Lys Ser Met Pro Glu Ser Pro Lys Asn Ser Thr Gln Ile
    370                 375                 380

Asp Pro Asn Glu Glu Gly Ser Ile Gly Tyr Val Lys Arg Val Val Glu
385                 390                 395                 400

Ser Met Glu Gln Thr Ser Pro Asn Pro Ser Glu Ile Ala Gln Arg Leu
                405                 410                 415

Gln Leu Asn Leu Ala Asn Ser Ser Gln His Ser Ser Ser Thr Ser Ile
            420                 425                 430

Thr Thr Pro Thr Asn Thr Pro Arg Asn Asn
```

-continued

```
      435                 440


<210> SEQ ID NO 23
<211> LENGTH: 31
<212> TYPE: DNA
<213> ORGANISM: Orientia tsutugamushi

<400> SEQUENCE: 23

tagtaggcac catgggtgga cagatgtctg a                                     31


<210> SEQ ID NO 24
<211> LENGTH: 32
<212> TYPE: DNA
<213> ORGANISM: Orientia tsutugamushi

<400> SEQUENCE: 24

ttgaataggg atcccaactt aattagcctg ac                                    32


<210> SEQ ID NO 25
<211> LENGTH: 32
<212> TYPE: DNA
<213> ORGANISM: Orientia tsutugamushi

<400> SEQUENCE: 25

ctctaataac catggtgatt gctggagatg at                                    32


<210> SEQ ID NO 26
<211> LENGTH: 33
<212> TYPE: DNA
<213> ORGANISM: Orientia tsutugamushi

<400> SEQUENCE: 26

ctgagggatc ctttgctaat tattgcgagg agt                                   33
```